US012084690B2

(12) United States Patent
Han et al.

(10) Patent No.: US 12,084,690 B2
(45) Date of Patent: Sep. 10, 2024

(54) RECOMBINANT HARSA THAT CROSSES THE BLOOD BRAIN BARRIER

(71) Applicant: LINNO PHARMACEUTICALS INC., Shanghai (CN)

(72) Inventors: Zhaozhong Han, Shanghai (CN); Hongya Pan, Shanghai (CN); Haiyang Li, Shanghai (CN); Lingyu Li, Shanghai (CN)

(73) Assignee: LINNO PHARMACEUTICALS INC., Shanghai (CN)

( * ) Notice: Subject to any disclaimer, the term of this patent is extended or adjusted under 35 U.S.C. 154(b) by 0 days.

(21) Appl. No.: 18/488,060

(22) Filed: Oct. 17, 2023

(65) Prior Publication Data

US 2024/0101981 A1 Mar. 28, 2024

Related U.S. Application Data

(63) Continuation-in-part of application No. PCT/CN2023/087490, filed on Apr. 11, 2023.

(30) Foreign Application Priority Data

Apr. 28, 2022 (CN) .......................... 202210459945.4

(51) Int. Cl.
| | | |
|---|---|---|
| *A61K 39/395* | (2006.01) | |
| *A61K 38/43* | (2006.01) | |
| *A61P 25/16* | (2006.01) | |
| *A61P 25/28* | (2006.01) | |
| *C07K 16/18* | (2006.01) | |
| *C12N 9/00* | (2006.01) | |
| *C12N 9/16* | (2006.01) | |
| *C12N 15/63* | (2006.01) | |

(52) U.S. Cl.
CPC ................ *C12N 9/16* (2013.01); *A61P 25/16* (2018.01); *A61P 25/28* (2018.01); *C07K 16/18* (2013.01); *C12N 15/63* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 2011/0092677 A1 | 4/2011 | Sadeghi et al. | |
| 2013/0142794 A1 | 6/2013 | Pardridge et al. | |
| 2017/0191041 A1 | 7/2017 | Radin | |
| 2019/0352624 A1 | 11/2019 | Matzner et al. | |

FOREIGN PATENT DOCUMENTS

| | | |
|---|---|---|
| CN | 105555310 A | 5/2016 |
| CN | 107849555 A | 3/2018 |
| CN | 109312367 A | 2/2019 |

OTHER PUBLICATIONS

International Search Report of PCT/CN2023/087490, mailed on Jul. 25, 2023.

*Primary Examiner* — Aurora M Fontainhas
(74) *Attorney, Agent, or Firm* — Jun He Law Offices P.C; Yi Zhang

(57) ABSTRACT

The present application pertains to a fusion protein, comprising a transferrin-binding protein, and an arylsulfatase A (ARSA) or functionally active fragment thereof, wherein the transferrin-binding protein comprises a peptide, an antibody or an antigen-binding fragment of the antibody capable of binding transferrin. The other aspect of the present application provides the preparing methods and the uses of the fusion protein.

18 Claims, 19 Drawing Sheets

Specification includes a Sequence Listing.

Figure 18A
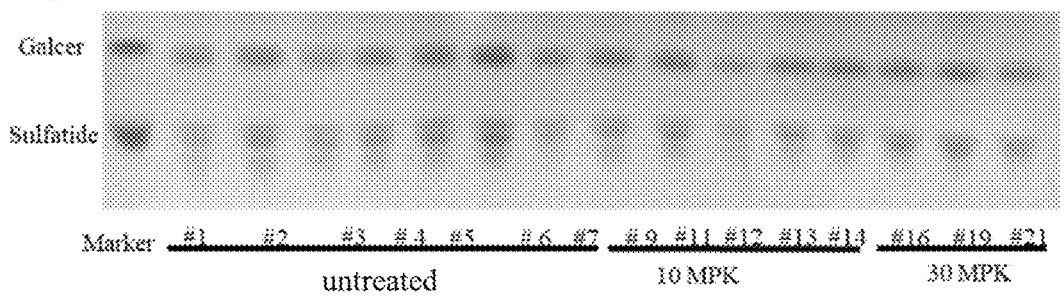
Figure 18B
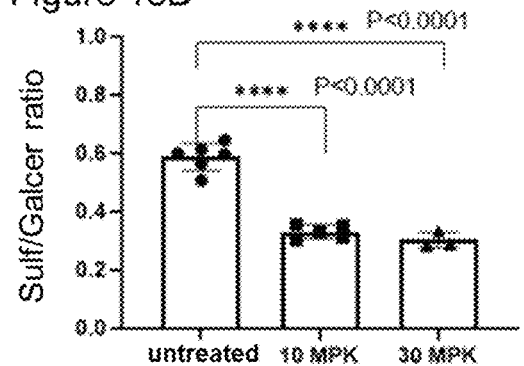
untreated     10 MPK     30 MPK
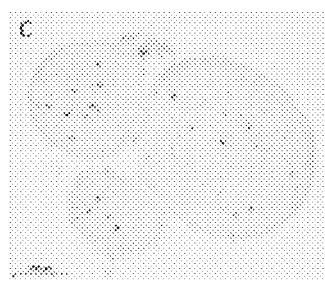 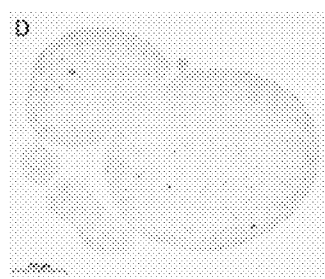 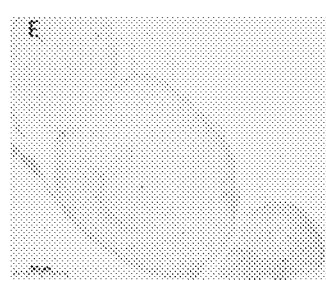
Figure 18C     Figure 18D     Figure 18E
Figure 18F
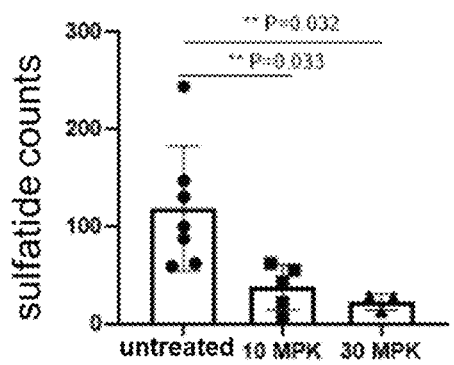

US 12,084,690 B2

RECOMBINANT HARSA THAT CROSSES THE BLOOD BRAIN BARRIER

CROSS-REFERENCE TO RELATED APPLICATIONS

The present application is a continuation-in-part application of PCT application no. PCT/CN2023/087490, filed Apr. 11, 2023, which claims priority to Chinese patent application 202210459945.4, filed Apr. 28, 2022, the contents of each of which are incorporated herein by reference in their entireties.

FIELD OF THE INVENTION

The present application relates to the field of biomedicine, specifically relating to a fusion protein comprising transferrin-binding protein and arylsulfatase A (ARSA), and uses thereof.

BACKGROUND

Arylsulfatase A (also known as ARSA, acylsulfatase A, or cerebroside-sulfatase) belongs to the class of lysosomal hydrolases. ARSA can break down sulfatide, namely hydrolyze "cerebroside 3-sulfate" into cerebroside and sulfate ions. ARSA mainly plays a biological role in lysosomes and participates in the metabolism of complex phospholipids. Meanwhile, in the cytoplasm of cells, the direct binding of ARSA enzyme and α-synuclein effectively prevents the protein aggregation and extracellular secretion of the latter. Thus, the absence or reduced activity of the ARSA enzyme is a direct cause of Metachromatic Leukodystrophy (MLD), a life-threatening lysosomal storage disorder. It is also associated with various neurodegenerative conditions like Parkinson's disease. Therefore, the replacement therapy of ARSA, particularly targeting the central nervous system, has the promise to provide necessary therapeutics for these diseases that seriously affect human life and health while currently have no effective treatment.

BRIEF SUMMARY OF THE INVENTION

The present application provides a fusion protein, comprising a transferrin-binding protein, and an arylsulfatase A (ARSA) or functionally active fragment thereof. The fusion protein described herein utilizes targeted transferrin single domain antibody technology and employs a protein or peptide segment fused with the single domain antibody. The fusion protein described herein retains a strong binding activity to transferrin while not interfering with the binding between transferrin and its receptor and possesses the ability to extend half-life and to cross the blood-brain barrier (BBB).

In one aspect, the present application provides a fusion protein, comprising (a) a transferrin-binding protein, and (b) an arylsulfatase A (ARSA) or functionally active fragment thereof, wherein the transferrin-binding protein comprises a peptide, an antibody or an antigen-binding fragment of the antibody capable of binding transferrin.

In certain embodiments, the fusion protein exhibits one or more properties selected from the group consisting of: capable of extending in vivo half-life of ARSA; capable of crossing blood brain barriers (BBB); capable of being delivered orally; capable of delivering the ARSA to a cell expressing transferrin receptor.

In certain embodiments, the transferrin is human transferrin.

In certain embodiments, the antibody is selected from the group consisting of: a single domain antibody, a monoclonal antibody, a chimeric antibody, a humanized antibody and a human antibody.

In certain embodiments, the antigen-binding fragment is selected from the group consisting of: Fab, Fab', Fv fragments, F(ab')2, F(ab)2, scFv, VHH, di-scFv and/or dAb.

In certain embodiments, the transferrin-binding protein is a VHH.

In certain embodiments, the transferrin-binding protein comprises a CDR3 having an amino acid sequence of SEQ ID NO: 3.

In certain embodiments, the transferrin-binding protein comprises a CDR2 having an amino acid sequence of SEQ ID NO: 2.

In certain embodiments, the transferrin-binding protein comprises a CDR1 having an amino acid sequence of SEQ ID NO: 1.

In certain embodiments, the transferrin-binding protein comprises a VHH having an amino acid sequence of SEQ ID NO: 8.

In certain embodiments, the ARSA is human ARSA.

In certain embodiments, the ARSA or the functionally active fragment thereof is an ARSA variant or the functionally active fragment thereof.

In certain embodiments, the ARSA or the functionally active fragment thereof comprises an amino acid sequence of SEQ ID NO: 10.

In certain embodiments, the transferrin-binding protein is directly or indirectly linked to the ARSA or the functionally active fragment thereof.

In certain embodiments, the N-terminal of the transferrin-binding protein is directly or indirectly linked to the C-terminal of the ARSA or the functionally active fragment thereof.

In certain embodiments, the C-terminal of the transferrin-binding protein is directly or indirectly linked to the N-terminal of the ARSA or the functionally active fragment thereof.

In certain embodiments, the transferrin-binding protein is linked to the ARSA or the functionally active fragment thereof through a linker moiety.

In certain embodiments, the linker moiety comprises a peptide linker.

In certain embodiments, the linker moiety comprises an amino acid sequence of SEQ ID NO: 9.

In certain embodiments, the fusion protein comprises an amino acid sequence of SEQ ID NO: 11.

In certain embodiments, the fusion protein is capable of binding transferrin and catalyzing the degradation of cerebroside sulfate which is a substrate of the ARSA.

In another aspect, the present application provides one or more isolated nucleic acid molecules encoding the fusion protein described herein.

In another aspect, the present application provides a vector comprising the nucleic acid molecule described herein.

In another aspect, the present application provides a cell comprising the nucleic acid molecule and/or the vector described herein.

In another aspect, the present application provides a pharmaceutical composition comprising the fusion protein described herein and a pharmaceutically acceptable carrier.

In another aspect, the present application provides a pharmaceutical composition comprising the fusion protein described herein, the nucleic acid molecule described herein, the vector described herein or the cell described herein, and optionally a pharmaceutically acceptable carrier.

In another aspect, the present application provides a method for preparing the fusion protein described herein, comprising culturing the cells described herein under conditions suitable for the fusion protein expression.

In another aspect, the present application provides a use of the fusion protein described herein, the nucleic acid molecule described herein, the vector described herein, the cell described herein, and/or the pharmaceutical composition described herein in the manufacture of a medicament for preventing and/or treating diseases and/or disease-related symptoms.

In certain embodiments, the diseases and/or disease-related symptoms comprise diseases and/or disease-related symptom caused by ARSA abnormalities.

In certain embodiments, the diseases and/or disease-related symptoms comprise neurological disorders caused by deposition of cerebroside sulfate substrate.

In certain embodiments, the disease is Metachromatic Leukodystrophy (MLD).

In certain embodiments, the disease is neurodegenerative disease.

In certain embodiments, the disease is Parkinson's disease.

In another aspect, the present application provides a method for preventing and/or treating diseases and/or disease-related symptoms, comprising administering to a subject in need thereof the fusion protein described herein, the nucleic acid molecule described herein, the vector described herein, the cell described herein and/or the pharmaceutical composition described herein.

In certain embodiments, the diseases and/or disease-related symptoms comprise diseases and/or disease-related symptom caused by ARSA abnormalities.

In certain embodiments, the diseases and/or disease-related symptoms comprise neurological disorders caused by deposition of cerebroside sulfate substrate.

In certain embodiments, the disease is selected from the group consisting of Metachromatic Leukodystrophy (MLD), neurodegenerative disease and Parkinson's disease.

In certain embodiments, the disease is Metachromatic Leukodystrophy (MLD).

In certain embodiments, the disease is neurodegenerative disease.

In certain embodiments, the disease is Parkinson's disease.

In another aspect, the present application provides the fusion protein described herein, the nucleic acid molecule described herein, the vector described herein, the cell described herein, and/or the pharmaceutical composition described herein, for use in the prevention and/or treatment of diseases and/or disease-related symptoms.

In certain embodiments, the diseases and/or disease-related symptoms comprise diseases and/or disease-related symptom caused by ARSA abnormalities.

In certain embodiments, the diseases and/or disease-related symptoms comprise neurological disorders caused by deposition of cerebroside sulfate substrate.

In certain embodiments, the disease is Metachromatic Leukodystrophy (MLD).

In certain embodiments, the disease is neurodegenerative disease.

In certain embodiments, the disease is Parkinson's disease.

In another aspect, the present application provides a method for delivering an ARSA to cross the BBB, comprising administering the fusion protein described herein.

In another aspect, the present application provides a method for extending in vivo half-life of an ARSA, comprising administering the fusion protein described herein.

From the detailed description provided in the following text, skilled persons in the field can easily discern other aspects and advantages of the present application. The subsequent detailed description only presents and describes exemplary embodiments of the application. As a skilled person in the field would recognize, the disclosure of the present application allows for modifications to the specific embodiments disclosed herein without departing from the spirit and scope of the invention. Accordingly, the descriptions in the figures and the specification of the application are exemplary and not limiting.

BRIEF DESCRIPTION OF THE DRAWINGS

The specific features of the invention disclosed herein are as shown in the attached claims. By referring to the detailed description of exemplary embodiments and the drawings provided in the following text, one can better understand the characteristics and advantages of the invention disclosed herein. A brief description of the drawings is as follows:

FIGS. 18A-18F show the TLC/ABS staining detection of cerebroside sulfate substrate levels in the sciatic nerve of mARSA-deficient mice after treatment with hARSA-9056VHH.

DETAILED DESCRIPTION OF THE INVENTION

Figure 1A:
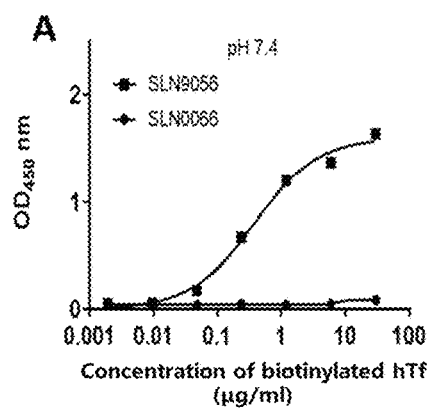
FIGS. 1A-1D show that the single domain antibody VHH targeting transferrin significantly prolongs the half-life of recombinant ovalbumin in mouse blood and enhances its ability to cross the BBB.

The following specific examples illustrate the implementation of the present application. Persons skilled in the art can easily understand other advantages and effects of the present application from the disclosed content in this specification.

Definition

As used herein, the term "fusion protein" generally refers to a protein obtained by fusing two or more proteins or peptides. Fusion proteins can be artificially prepared using recombinant DNA technology. For example, genes or nucleic acid molecules encoding the two or more proteins or peptides can be linked together to form a fusion gene or fusion nucleic acid molecule, which encodes the said fusion protein. Translation of the fusion gene can produce a single polypeptide that possesses the properties of at least one or even every protein or peptide fused before.

As used herein, the term "transferrin" generally refers to a glycoprotein capable of binding and transporting multivalent ions. For example, transferrin can be a monomeric glycoprotein and may have at least one ion-binding site. The ion-binding sites can exhibit different affinities for ions. The multivalent ions can be iron ions, chromium ions, manganese ions, cadmium ions, or nickel ions. In some embodiments, each transferrin can bind two trivalent iron atoms. Transferrin can exist in its iron-bound form as holo-transferrin or its iron-free form as apo-transferrin. Examples of transferrin can include mouse transferrin and human transferrin. For example, the amino acid sequence of mouse transferrin can be specified in GenBank under accession numbers EDL21066.1, AAL34533.1, or AAL34533.1. Similarly, human transferrin can be referenced in GenBank under accession numbers AAH59367.1, AAH59367.1, or AAB22049.1. As used herein, the term "transferrin" can encompass its functional active fragments, homologs, analogs, and/or variants.

As used herein, the term "transferrin-binding protein" generally refers to a protein containing the transferrin-binding domain and may optionally allow the antigen-binding portion to adopt a scaffold or framework that promotes antigen binding. For example, the transferrin-binding protein described herein can include but is not limited to antibodies, antigen-binding fragments (Fab, Fab', F(ab)2, Fv fragments, F(ab')2, VHH, scFv, di-scFv, and/or dAb), immune complexes, multispecific antibodies, antibody fragments, antibody derivatives, antibody analogs, or fusion proteins, as long as they exhibit the desired antigen-binding activity. The antigen-binding protein can specifically bind to transferrin, and it may not interfere with the interaction between transferrin and transferrin receptor 1 (TfR1). The transferrin-binding protein can retain the normal physiological function of iron transport.

As used herein, the term "antibody" generally refers to a protein containing one or more polypeptides encoded substantially by immunoglobulin genes or immunoglobulin gene segments. Immunoglobulin genes can include κ, λ, α, γ, δ, ε, and μ constant region genes, as well as numerous immunoglobulin variable region genes. The light chains can be classified as κ or λ, defining the immunoglobulin types: Igκ and Igλ, respectively. The heavy chains can be classified as γ, μ, α, δ, or ε, defining the immunoglobulin classes: IgG, IgM, IgA, IgD, and IgE, respectively. Antibodies may have a quaternary structure, where each quaternary can be composed of two pairs of identical polypeptide chains, with each pair consisting of a "light" chain (approximately 25 kD) and a "heavy chain" (approximately 50-70 kD). The N-terminus of each chain may define approximately 100 to 110 or more amino acids of the variable region, which is primarily responsible for antigen recognition. The terms "light chain variable region (VL)" and "heavy chain variable region (VH)" generally refer to the variable region regions of the light and heavy chains, respectively. Antibodies can exist as complete immunoglobulins or as fully characterized fragments produced by digestion with various peptidases or expressed from scratch. In certain embodiments, the antibody used herein may consist solely of the heavy chain variable region. For example, the antibody can be a single-domain antibody.

As used herein, the term "antigen-binding fragment" generally refers to one or more portions of the full-length antibody that substantially retain the ability to bind to the same antigen (e.g., CD38) as the full-length antibody. In some embodiments, the antigen-binding fragment can compete with the full-length antibody for specific binding to the antigen. For further details, reference may be made to Fundamental Immunology, Ch. 7 (Paul, W., ed., 2nd edition, Raven Press, N.Y. (1989)), and the entire text is incorporated herein by reference. Antigen-binding fragments can be produced by recombinant DNA technology or by enzymatic or chemical cleavage of complete antibodies. In some embodiments, antigen-binding fragments include Fab, Fab', F(ab')$_2$, (Fab)$_2$, Fd, Fv, dAb, complementary determining region (CDR) fragments, VHH, single-chain antibodies (e.g., scFv), chimeric antibodies, diabodies, and such peptides that contain at least a portion of the antibody that confers specific antigen-binding ability. Antigen-binding fragments of a given antibody can be obtained from the antibody using conventional techniques known to those skilled in the art (e.g., recombinant DNA technology or enzymatic or chemical cleavage), and they can be screened for specificity in the same way as for intact antibodies. For example, pepsin can digest antibody portion following disulfide bonds in hinge regions to produce F(ab')$_2$.

As used herein, the term "VHH" generally refers to an antibody that contains the variable antigen-binding domain of the heavy chain (see Vanlandschoot et al., 2011, Antiviral Research 92, 389-407). VHH is also known as a "Nanobody" (Nb) and/or a single-domain antibody.

As used herein, the terms "Arylsulfatase A" and "ARSA" can be used interchangeably and encompass both the wild-type ARSA and modified ARSA. For example, ARSA can include its homologs, analogs, derivatives, and/or functional variants.

In some embodiments, ARSA can include the full-length ARSA or functional activity fragment thereof. In some embodiments, ARSA is human ARSA ("hARSA"). In some embodiments, ARSA is recombinant human ARSA ("rhARSA").

As used herein, the term "functional activity fragment" generally refers to a partial region of a full-length protein or nucleic acid that retains or partially retains the biological activity or function of the full-length protein or nucleic acid. For example, a functional activity fragment can retain or partially retain the ability of the full-length protein to bind to another molecule. For instance, a functional activity fragment of Arylsulfatase A (ARSA) can retain or partially retain the biologically active function of the full-length ARSA that causes cell proliferation.

As used herein, the term "Fab" generally refers to an antibody fragment consisting of VL, VH, CL, and CH1 domains.

As used herein, the term "Fab" generally refers to an antibody fragment that has several additional residues at the carboxy-terminal end of the CH1 domain compared to the Fab fragment. For example, Fab' may include one or more cysteine residues from the antibody hinge region.

As used herein, the term "F(ab)$_2$" generally refers to an antigen-binding fragment obtained by linking pairs of Fab fragments with cysteine.

As used herein, the term "dAb fragment" generally refers to an antibody fragment consisting of VH domain(s) (Ward et al., Nature 341: 544-546, 1989).

As used herein, the term "complementarity-determining region (CDR)" generally refers to the three hypervariable regions (HVRs) in the light chain variable region (VL) and heavy chain variable region (VH) of the light and heavy chain, respectively, which form precise complementary interactions with antigen determinants in the spatial structure. Therefore, the hypervariable region is also named the complementarity-determining region.

As used herein, the term "Fv fragment" generally refers to an antibody fragment composed of the single-arm VL and VH domains of an antibody.

As used herein, the term "scFv" also known as a single-chain antibody generally refers to a molecule formed by connecting the heavy chain variable region and the light chain variable region of an antibody through a short peptide linker.

As used herein, the mentioned proteins, peptides, and/or amino acid sequences should also be understood to include variants or homologs that have the same or similar functions as the specified protein or peptide.

As used herein, the term "variant" of a protein or polypeptide may refer to a molecule has one or more amino acid substitutions, deletions, or additions in the amino acid sequence of the protein or the polypeptide. For example, a functional variant of a protein or polypeptide may contain at least one amino acid substitution, deletion, and/or insertion, for example, 1-30, 1-20, or 1-10 amino acids, such as 1, 2, 3, 4, or 5 amino acids substitutions, deletions, and/or insertions, as compared to the amino acid sequence of the protein or polypeptide. The functional variant of a protein or polypeptide may substantially retain the biological characteristics of the protein or polypeptide without the changes (e.g., substitutions, deletions, or additions). For instance, the functional variant of a protein or polypeptide may retain at least 60%, 70%, 80%, 90%, or 100% of the biological activity (e.g., antigen-binding capability) of the protein or polypeptide without the changes. The substitutions may be conservative substitutions.

As used herein, the term "sequence homology" generally refers to the similarity or interchangeability between two or more polynucleotide sequences or two or more polypeptide sequences. When determining the sequence identity, similarity, or homology between two different amino acid sequences using programs such as Emboss Needle or Best-Fit, default settings may be used, or appropriate scoring matrices (such as blosum45 or blosum80) may be chosen to optimize the identity, similarity, or homology scores. In some implementations, sequence-homologous polynucleotides are those sequences that hybridize under stringent conditions and have at least 60%, at least 65%, at least 70%, at least 80%, at least 90%, at least 95%, at least 97%, at least 98%, at least 99%, or even 100% sequence identity. When aligning sequences of considerable length, sequence-homologous peptides may have at least 80%, at least 90%, at least 95%, at least 97%, at least 98%, or at least 99% sequence identity.

Usually, an amino and a carboxyl in a polypeptide chain can be joined to form a chain. At both ends of a protein, there are residues of amino acid left over without forming peptide bonds, respectively, being a polypeptide chain end carrying free amino and a polypeptide chain end carrying a carboxyl. As used herein, the term "N-terminal" generally refers to the end of the polypeptide chain carrying a free amino in the terminal amino acid residue. As used herein, the term "C-terminal" generally refers to the end of the polypeptide chain carrying a free carboxyl in the terminal amino acid residue.

The term "nucleic acid molecule" or "nucleic acid" or "polynucleotides" can be used interchangeably herein. The term "nucleic acid molecule" generally refers to a deoxyribonucleic acid (DNA), or ribonucleic acid (RNA), or analogs thereof in any length, which is isolated from natural environments or artificially synthesized.

As used herein, the term "vector" generally refers to a nucleic acid carrier that allows a polynucleotide encoding a protein of interest to be inserted in it and expressed. Vectors can be transformed, transduced, or transfected into host cells, allowing the carried genetic elements thereinto be expressed in host cells. For example, vectors include plasmids, bacteriophages, cosmid, artificial chromosomes such as yeast artificial chromosomes (YAC), bacterial artificial chromosomes (BAC), or P1-derived artificial chromosomes (PAC), phages such as λ-phage or M13-phage, and animal viruses. Animal viruses used as vectors include retroviruses (including lentiviruses), adenoviruses, adeno-associated viruses, herpesviruses (such as herpes simplex virus), poxviruses, papillomaviruses, and polyomaviruses (such as SV40). A vector may contain multiple regulatory elements, including promoter sequences, transcription initiation sequences, enhancer sequences, selection elements, and reporter genes. In addition, a vector may include a replication origin. A vector may also contain components that assist its entry into cells, such as viral particles, liposomes, or protein shells, among others.

As used herein, the term "pharmaceutical composition" generally refers to a mixture of active ingredient(s) with other chemical or biological components, such as pharmaceutically acceptable diluent, excipient or carrier, which allow the biological activity of the active ingredient(s) to be effective in a subject and/or facilitate administration of the active ingredient(s) to a subject. The pharmaceutical composition can be sterile.

As used herein, the term "pharmaceutically acceptable carrier" generally refers to any and all solvents, dispersion media, coatings, antibacterial and antifungal agents, isotonic and absorption delaying agents, and the like, that are compatible with pharmaceutical administration and suitable for use in tissues without undue toxicity, irritation, allergic reactions, or other problems or complications. The utilization of the pharmaceutical carrier has a reasonable benefit/risk ratio based on sound medical judgment. For example, pharmaceutically acceptable carrier may refer to those adjuvants that are approved by regulatory agencies (such as the US Food and Drug Administration, China Food and Drug Administration, or European Medicines Agency) or listed in widely recognized pharmacopeias (such as the US Pharmacopeia, China Pharmacopeia, or European Pharmacopoeia) for use in animals (more particularly for use in humans).

The articles "a" and "an" used herein, unless clearly indicated to the contrary, should be understood to include the plural referents.

As used herein, the term "comprise", "include", "encompass", "contain", and "embrace" can be used interchangeably.

As used herein, the term "about" generally means varying by 0.5%-10% above or below the specified value, for example, varying by 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10.

Fusion Proteins

In one aspect, the present application provides a fusion protein, comprising a transferrin-binding protein and an arylsulfatase A (ARSA) or functionally active fragment thereof. For example, the transferrin-binding protein comprises a peptide, an antibody or an antigen-binding fragment of the antibody capable of binding transferrin.

In some embodiments, the fusion protein exhibits one or more properties. For example, the fusion protein is able to extend in vivo half-life of ARSA. For example, the fusion protein is able to cross blood brain barriers (BBB). For example, the fusion protein is able to be delivered orally. For example, the fusion protein is able to deliver the ARSA to a cell expressing transferrin receptor.

In some embodiments, the fusion protein can be human transferrin.

In some embodiments, the antibody capable of binding transferrin is selected from the group consisting of: a single domain antibody, a monoclonal antibody, a chimeric antibody, a humanized antibody and a human antibody.

In some embodiments, the antigen-binding fragment capable of binding transferrin is selected from the group consisting of: Fab, Fab', Fv fragments, F(ab')$_2$, F(ab)$_2$, scFv, VHH, di-scFv and/or dAb.

In some embodiments, the transferrin-binding protein comprises VHH capable of binding transferrin.

For example, the transferrin-binding protein comprises at least one CDR of a VHH. In some embodiments, the VHH has an amino acid sequence of SEQ ID NO: 8.

As used herein, the "complementarity-determining region" (CDRs) of an antibody, also known as hypervariable regions, are part of the variable region. The amino acid residues in this region can interact with the antigen or antigenic epitope. The CDRs of an antibody can be determined using various encoding systems, such as CCG, Kabat, Chothia, IMGT, AbM, or a combination of Kabat/Chothia. These encoding systems are well-known in the field and can be found, for example, at http://www.bioinf.org.uk/abs/index.html#kabatnum. Persons skilled in the art can determine the CDR regions based on the antibody's sequence and structure using different encoding systems, which may result in some differences. As used herein, the term "CDR" includes CDR sequences obtained through any CDR delineation method. It also includes variants of the CDR, where the amino acid sequence of the CDR undergoes one or more substitutions, deletions, and/or additions of, for example, 1-30, 1-20, or 1-10 amino acids, or even 1, 2, 3, 4, 5, 6, 7, 8, or 9 amino acids. Additionally, it includes homologs of the CDR, where the homologous sequence shares at least about 85% (e.g., at least about 85%, about 90%, about 91%, about 92%, about 93%, about 94%, about 95%, about 96%, about 97%, about 98%, about 99%, or higher) sequence identity with the amino acid sequence of the CDR. In some implementations, the CDR of the transferrin-binding protein in the present application can be defined using the Kabat encoding system.

In some embodiments, the transferrin-binding protein comprises a CDR3 having an amino acid sequence of SEQ ID NO: 3.

In some embodiments, the transferrin-binding protein comprises a CDR2 having an amino acid sequence of SEQ ID NO: 2.

In some embodiments, the transferrin-binding protein comprises a CDR1 having an amino acid sequence of SEQ ID NO: 1.

In some embodiments, the transferrin-binding protein comprises CDR1, CDR2 and CDR3, wherein the CDR1 has an amino acid sequence of SEQ ID NO: 1, the CDR2 has an amino acid sequence of SEQ ID NO: 2 and the CDR3 has an amino acid sequence of SEQ ID NO: 3.

In some embodiments, the transferrin-binding protein comprises a framework region 1 (FR1) of a VHH, wherein the FR1 has an amino acid sequence of SEQ ID NO: 4. In some embodiments, the transferrin-binding protein comprises a framework region 2 (FR2) of a VHH, wherein the FR1 has an amino acid sequence of SEQ ID NO: 5. In some embodiments, the transferrin-binding protein comprises a framework region 3 (FR3) of a VHH, wherein the FR1 has an amino acid sequence of SEQ ID NO: 6. In some embodiments, the transferrin-binding protein comprises a framework region 4 (FR4) of a VHH, wherein the FR1 has an amino acid sequence of SEQ ID NO: 7.

In some embodiments, the transferrin-binding protein comprises a VHH capable of binding transferrin, and wherein the VHH has an amino acid sequence of SEQ ID NO: 8.

In some embodiments, the ARSA or the functionally active fragment thereof can be human ARSA or the functionally active fragment thereof. In some embodiments, the ARSA or the functionally active fragment can be modified to retain the function and/or activity of ARSA.

In some embodiments, the ARSA or the functionally active fragment thereof comprises an amino acid sequence of SEQ ID NO: 10.

In some embodiments, the ARSA or the functionally active fragment thereof as used herein is an ARSA variant or the functionally active fragment thereof, an ARSA truncated body or the functionally active fragment thereof, an ARSA homolog or the functionally active fragment thereof, or an ARSA analogue or the functionally active fragment thereof. In some embodiments, the ARSA or the functionally active fragment thereof may also have an amino acid sequence having at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 99.9% sequence identity with the amino acid sequence as set forth in SEQ ID NO: 10. In some embodiments, the ARSA or its functional activity fragment may have an amino acid sequence that differs from SEQ ID NO: 10 by 1, 2, 3, 4, 5, 6, 7, 8, 9, 10, 11, 12, 13, 14, 15, 16, 17, 18, 19, 20, 25, 30, or more amino acid mutations.

In some embodiments, in the fusion protein, the transferrin-binding protein is directly or indirectly linked to the ARSA or the functionally active fragment thereof.

In some embodiments, in the fusion protein, the N-terminal of the transferrin-binding protein is directly or indirectly linked to the C-terminal of the ARSA or the functionally active fragment thereof.

In some embodiments, in the fusion protein, the C-terminal of the transferrin-binding protein is directly or indirectly linked to the N-terminal of the ARSA or the functionally active fragment thereof.

In some embodiments, in the fusion protein, the transferrin-binding protein is linked to the ARSA or the functionally active fragments thereof through a linker moiety. For example, the linker moiety comprises a flexible linker. For example, the linker moiety comprises a peptide linker.

In some embodiments, in the fusion protein, the linker moiety comprises an amino acid sequence of SED ID NO: 9.

In some embodiments, the fusion protein comprises an amino acid sequence of SED ID NO: 11.

In some embodiments, the fusion protein is capable of binding transferrin and catalyzing the degradation of cerebroside sulfate which is a substrate of the ARSA.

TABLE 1

Sequences

| SEQ ID NO: | LABEL | NOTE | TYP | ORG | SEQ |
|---|---|---|---|---|---|
| 1 | SLN9056 HCDR1 | SLN9056 HCDR1 | PRT | Synthetic construct | GNYMG |
| 2 | SLN9056 HCDR2 | SLN9056 HCDR2 | PRT | Synthetic construct | VLYTGGGSTYYADSVKG |
| 3 | SLN9056 HCDR3 | SLN9056 HCDR3 | PRT | Synthetic construct | ALGSARWYTSSLDARAYNI |
| 4 | SLN9056 H-FR1 | SLN9056 H-FR1 | PRT | Synthetic construct | EVQLVESGGGLVQPGGSLRLSCAASGHAYG |
| 5 | SLN9056 H-FR2 | SLN9056 H-FR2 | PRT | Synthetic construct | WFRQAPGKGLEGVA |
| 6 | SLN9056 H-FR3 | SLN9056 H-FR3 | PRT | Synthetic construct | RFTISEDNSKNTVYLQMNSLRAEDTAVYYCAL |
| 7 | SLN9056 H-FR4 | SLN9056 H-FR4 | PRT | Synthetic construct | WGQGTLVTVSS |
| 8 | SLN9056 VHH | SLN9056 VHH | PRT | Synthetic construct | EVQLVESGGGLVQPGGSLRLSCAASGHAYGGNY MGWFRQAPGKGLEGVAVLYTGGGSTYYADSVK GRFTISEDNSKNTVYLQMNSLRAEDTAVYYCAL ALGSARWYTSSLDARAYNIWGQGTLVTVSS |
| 9 | Linker | linker | PRT | Synthetic construct | GGGGSGGGGSGGGGS |
| 10 | hARSA | hARSA | PRT | Synthetic construct | RPPNIVLIFADDLGYGDLGCYGHPSSTTPNLDQL AAGGLRFTDFYVPVSLCTPSRAALLTGRLPVRMG MYPGVLVPSSRGGLPLEEVTVAEVLAARGYLTG MAGKWHLGVGPEGAFLPPHQGFHRFLGIPYSHD QGPCQNLTCFPPATPCDGGCDQGLVPIPLLANLS VEAQPPWLPGLEARYMAFAHDLMADAQRQDRP FFLYYASHHTHYPQFSGQSFAERSGRGPFGDSLM ELDAAVGTLMTAIGDLGLLEETLVIFTADNGPET MRMSRGGCSGLLRCGKGTTYEGGVREPALAFW PGHIAPGVTHELASSLDLLPTLAALAGAPLPNVTL DGFDLSPLLLGTGKSPRQSLFFYPSYPDEVRGVFA VRTGKYKAHFFTQGSAHSDTTADPACHASSSLT AHEPPLLYDLSKDPGENYNLLGGVAGATPEVLQ ALKQLQLLKAQLDAAVTFGPSQVARGEDPALQI CCHPGCTPRPACCHCPDPHA |
| 11 | hARSA-9056 | hARSA-9056 | PRT | Synthetic construct | RPPNIVLIFADDLGYGDLGCYGHPSSTTPNLDQL AAGGLRFTDFYVPVSLCTPSRAALLTGRLPVRMG MYPGVLVPSSRGGLPLEEVTVAEVLAARGYLTG MAGKWHLGVGPEGAFLPPHQGFHRFLGIPYSHD QGPCQNLTCFPPATPCDGGCDQGLVPIPLLANLS VEAQPPWLPGLEARYMAFAHDLMADAQRQDRP FFLYYASHHTHYPQFSGQSFAERSGRGPFGDSLM ELDAAVGTLMTAIGDLGLLEETLVIFTADNGPET |

TABLE 1-continued

Sequences

| SEQ ID NO: | LABEL | NOTE | TYP | ORG | SEQ |
|---|---|---|---|---|---|
| | | | | | MRMSRGGCSGLLRCGKGTTYEGGVREPALAFW PGHIAPGVTHELASSLDLLPTLAALAGAPLPNVTL DGFDLSPLLLGTGKSPRQSLFFYPSYPDEVRGVFA VRTGKYKAHFFTQGSAHSDTTADPACHASSSLT AHEPPLLYDLSKDPGENYNLLGGVAGATPEVLQ ALKQLQLLKAQLDAAVTFGPSQVARGEDPALQI CCHPGCTPRPACCHCPDPHAGGGGSGGGGSGGG GSEVQLVESGGGLVQPGGSLRLSCAASGHAYGG NYMGWFRQAPGKGLEGVAVLYTGGGSTYYADS VKGRFTISEDNSKNTVYLQMNSLRAEDTAVYYC ALALGSARWYTSSLDARAYNIWGQGTLVTVSSG GGGSHHHHHH |
| 12 | SLN0066 | SLN0066 | PRT | Synthetic construct | HVQLVESGGGSVQAGGSLRLSCVASGIGHGFNN NCMGWFRQAPGKEREGVAAVYTGGGTPYYADS VKGRFTLSQDNAKNTLYLQMNGLDPEDTAMYY CVADIWRTYRCGAGDTTVFDYRGQGTLVTVSS |

Nucleic Acid Molecules, Carriers, Cells, Pharmaceutical Compositions, Methods of Preparation In another aspect, the present application provides one or more isolated nucleic acid molecules encoding the fusion protein described herein.

The nucleic acid molecule described herein may be isolated. For example, the nucleic acid molecule may be generated or synthesized by following methods: (i) in vitro amplification, such as polymerase chain reaction (PCR) amplification, (ii) recombinant cloning techniques, (iii) purification, for instance, by enzyme digestion and gel electrophoresis, or (iv) chemically synthesis.

Recombinant DNA and molecular cloning techniques, including those described by Sambrook, J., Fritsch, E. F., and Maniatis, T. in "Molecular Cloning: A Laboratory Manual," Cold Spring Harbor Laboratory Press: Cold Spring Harbor (1989) (Maniatis), and by T. J. Silhavy, M. L. Bennan, and L. W. Enquist in "Experiments with Gene Fusions," Cold Spring Harbor Laboratory, Cold Spring Harbor, N.Y. (1984), and by Ausubel, F. M., et al. in "Current Protocols in Molecular Biology," pub. by Greene Publishing Assoc. and Wiley-Interscience (1987). In brief, nucleic acids can be prepared from genomic DNA fragments, cDNA, and RNA, all of which can be directly extracted from cells or produced through various amplification methods, including but not limited to PCR and RT-PCR.

Direct chemical synthesis of nucleic acids typically involves sequentially adding 3'-protected and 5'-protected nucleotide monomers to the 5'-hydroxyl end of the growing nucleotide polymer chain, where each addition is achieved by nucleophilic attack of the 3'-position of the added monomer on the 5'-hydroxyl end of the growing chain. The monomers are typically phosphoramidites, such as phosphorotriesters and phosphoramidites. See, for example, Matteuci et al., Tet. Lett. 521:719 (1980); U.S. Pat. Nos. 4,500,707, 5,436,327 and 5,700,637.

In another aspect, the present application provides a vector comprising the nucleic acid molecule described herein. The vector can be any linear nucleic acid, plasmids, phages, cosmids, RNA vectors, viral vectors, etc. Non-limiting examples of viral vectors include retroviruses, adenoviruses, and adeno-associated viruses.

In another aspect, the present application provides one or more vectors comprising the nucleic acid molecules described herein. Each vector may comprise one or more nucleic acid molecules described herein. In addition, the vector may comprise other genes, for example, marker genes that allow for the selection of the vector in appropriate host cells under suitable conditions. In addition, the vector may also comprise expression control elements that allow for proper expression of the coding region in the appropriate host cells. The control elements are well-known to persons skilled in the field and may include promoters, ribosome binding sites, enhancers, and other regulatory elements that control gene transcription or mRNA translation. In some embodiments, the expression control elements may be modifiable elements. The specific structure of the expression control elements may vary depending on the species or cell type's functionality, but typically comprises 5' untranslated sequences and 5' and 3' non-translated sequences involved in transcription and translation initiation, such as TATA box, cap sequences, CAAT sequences, and the like. For example, the 5' untranslated expression control sequence may comprise a promoter region that includes a promoter sequence for functional linkage with the nucleic acid controlling transcription. The expression control sequence may also comprise enhancer sequences or upstream activating sequences. The vector may comprise various types of carriers, such as plasmids, viral vectors, bacteriophages, yeast artificial chromosomes (YACs), bacterial artificial chromosomes (BACs), or other commonly used vectors in genetic engineering.

In another aspect, the present application provides a cell comprising the fusion proteins described herein, the nucleic acid molecules described herein, or the vectors described herein. The cell may be a host cell. For example, the cell may comprise various cell types, such as prokaryotic cells like *Escherichia coli* or Bacillus subtilis, fungal cells like yeast cells or Aspergillus cells, insect cells like S2 Drosophila cells or Sf9 cells, or animal cells such as fibroblasts, CHO cells, COS cells, NSO cells, HeLa cells, BHK cells, HEK 293 cells, or human cells.

For example, the stable or transient introduction of the vector into the host cell can be achieved using various established techniques. For example, a method involves calcium chloride treatment, wherein the vector is introduced through calcium precipitation. Other salts, such as calcium phosphate, can also be used similarly. In addition, electroporation can be employed, wherein an electric current is applied to increase the permeability of the cells to nucleic acids. Other examples of transformation methods include microinjection, DEAE-dextran-mediated transfection, and heat shock in the presence of lithium acetate. Lipid complexes, liposomes, and dendrimers can also be used for transfecting host cells.

In another aspect, the present application provides a method for preparing the fusion protein described herein, wherein the method may comprise culturing the cell described herein under conditions suitable for the fusion protein expression. For example, the method may comprise using appropriate media, appropriate temperature and incubation time, all of which are known to those of ordinary skill in the art.

In another aspect, the present application provides a composition comprising the fusion proteins described herein, the nucleic acid molecules described herein and optionally a pharmaceutically acceptable carrier.

For example, the pharmaceutically acceptable carrier may include buffers, antioxidants, preservatives, low molecular weight polypeptides, proteins, hydrophilic polymers, amino acids, sugars, chelating agents, counterions, metal complexes and/or nonionic surfactants, and the like.

In the present application, the compositions may be formulated with pharmaceutically acceptable carriers or diluents and any other known auxiliary agents and excipients according to conventional technical means in the art, such as according to Remington: The Science and Practice of Pharmacy, Nineteenth Edition, edited by Gennaro, Mack Publishing Co. of Easton, PA, 1995 for the techniques disclosed therein.

In the present application, the pharmaceutical composition may be formulated for oral administration in various forms, such as tablets, capsules, pills, powders, sustained-release formulations, solutions, and suspensions. The pharmaceutical composition may be a unit dosage form suitable for precise single-dose administration. The pharmaceutical composition may also comprise conventional drug carriers or excipients. In addition, the pharmaceutical composition may include other drugs or therapeutics, carriers, adjuvants, etc.

The pharmaceutical composition described herein may comprise a therapeutically effective amount of the fusion proteins described herein. The therapeutically effective amount refers to the dosage that is sufficient to prevent and/or treat (at least partially treat) the symptoms or conditions (e.g., neurodegenerative diseases) and/or any complications in a subject having or at risk of developing such conditions. The specific quantity/concentration of the dosage can vary based on the method of administration and the patient's needs, and may be determined based on factors such as patient volume, viscosity, and/or body weight. It should be understood that healthcare professionals (e.g., physicians or pharmacists) can easily adjust these specific dosages based on the specific patient, formulation, and/or condition.

Use

In another aspect, the present application provides use of the fusion proteins described herein, the nucleic acid molecules described herein, the vectors described herein, the cells described herein and/or the pharmaceutical compositions described herein in the manufacture of a medicament, wherein the medicament is used for preventing and/or treating diseases and/or disease-related symptoms.

In another aspect, the present application provides a method for preventing and/or treating diseases and/or disease-related symptoms, comprising administrating the fusion proteins described herein, the nucleic acid molecules described herein, the vectors described herein, the cells described herein and/or the pharmaceutical compositions described herein to a subject in need.

In another aspect, the present application provides the fusion proteins described herein, the nucleic acid molecules described herein, the vectors described herein, the cells described herein, and/or the pharmaceutical compositions described herein, for use in the prevention and/or treatment diseases and/or disease-related symptoms.

In some embodiments, the diseases and/or disease-related symptoms comprise diseases and/or disease-related symptom caused by ARSA abnormalities.

In some embodiments, the diseases and/or disease-related symptoms comprise neurological disorders caused by deposition of cerebroside sulfate substrate.

In some embodiments, the diseases and/or disease-related symptoms comprise Metachromatic Leukodystrophy (MLD).

In some embodiments, the diseases and/or disease-related symptoms comprise Parkinson's disease.

In another aspect, the present application provides a method for delivering a medicament to cross the BBB, comprising administering the fusion protein described herein.

In another aspect, the present application provides a method for extending in vivo half-life of an ARSA, comprising administering the fusion protein described herein.

Without wishing to be limited by any theory, the embodiments hereinafter are intended only to better illustrate the fusion proteins, methods of preparation, uses, etc. of the present application, and are not intended to limit the scope of the invention of the present application

EXAMPLES

Example 1 Discovery of Single Domain Antibody (VHH) Specific to Transferrin

Two 2-3 years old Asian alpacas were immunized with purified human transferrin obtained from human plasma. The specific serum titer was at least 1:10000 or higher by ELISA. Two hundred milliliters of peripheral blood were collected for isolating and purifying mononuclear cells (PBMCs). mRNA was extracted from PBMCs, reverse transcribed into cDNA, and then amplified with VHH-specific primers. The amplified sequences were cloned into a phage display vector to construct a VHH phage display library. Based on the results of sequencing, approximately 100 randomly selected clones were estimated. The constructed phage display library had an effective capacity of approximately one billion ($10^9$) independent VHH sequences.

Liquid-phase screening of VHH phage display library: one to ten micrograms of biotinylated human transferrin were incubated with $10^{12}$ CFU (cloning forming unit) phages in phosphate-buffered saline containing 1% bovine serum albumin and 0.05% Tween 20 (PBST-1% BSA) for 1 hour. Then, PBST-1% BSA pre-washed, blocked and streptavidin-conjugated magnetic beads (Invitrogen, Dynabeads M-280 streptavidin) were added. After incubating at room temperature for 1 hour, the magnetic beads bound with phages were washed 10 times with PBST. The phages were eluted by trypsin at 10 µg/mL. *Escherichia coli* were infected for amplification, and used for the next round of screening or for picking up single clones for ELISA screening. Also used for selecting VHH sequences that specifically bind to human transferrin without affecting the binding of transferrin to its receptor.

Figure 1B:
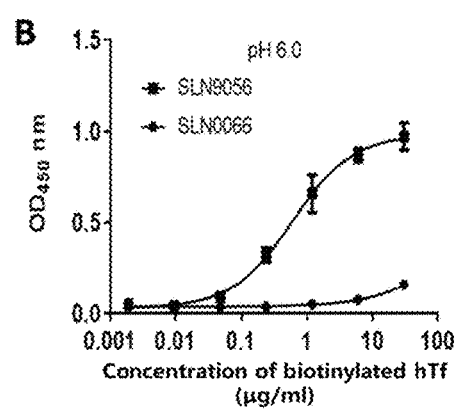
Figure 1C:
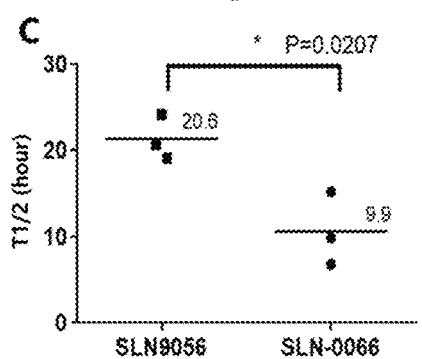
Figure 1D:
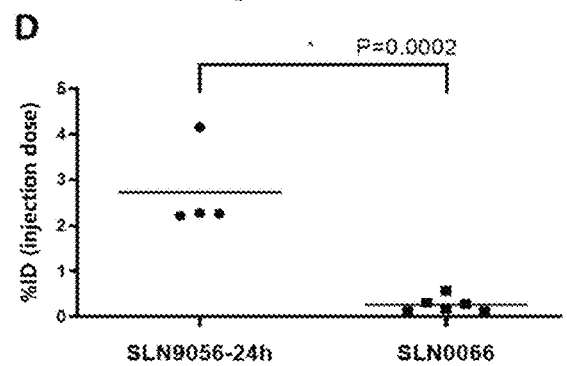

Among the obtained specific VHH sequences, SLN9056 (amino acid sequences of its CDR1, CDR2, and CDR3 are set forth in SEQ ID NO: 1, SEQ ID NO: 2, and SEQ ID NO: 3, respectively, and the amino acid sequence of its VHH is set forth in SEQ ID NO: 8) exhibited better human transferrin binding activity (both at pH7.4 and pH6.0) (FIG. 1A and FIG. 1B). The half-life of the recombinant ovalbumin (OVA) fusions, which include SLN9056, was significantly prolonged in mouse blood (FIG. 1C). Mice were intravenously injected with purified recombinant proteins (VHH-OVA-His) at a dose of 10 mg/kg. These treated mice were also intraperitoneally supplied with 10 mg/kg human transferrin daily, commencing one day prior to the administration of the aforesaid purified recombinant proteins. At different time points after dosing, brain samples were collected by perfusing with 20 mL of PBS and then frozen in liquid nitrogen. ELISA was used to quantify the amount of VHH-OVA-His in brain homogenates. Rabbit anti-OVA polyclonal antibodies (Sigma C6534-2 ml) were used for coating, and biotinylated rabbit anti-VHH antibodies (GeneScript, A02015-200) were used for detection. Compared to the negative control (SLN0066, a VHH can't bind with transferrin, with amino acid sequence set forth in SEQ ID NO: 12), the VHHs which binds to transferrin significantly increases the concentration of the test articles in brain tissue (for the selected VHH, the average % ID (injection dose) were between ~1.03% to ~3.5%) (FIG. 1D).

Figure 2:
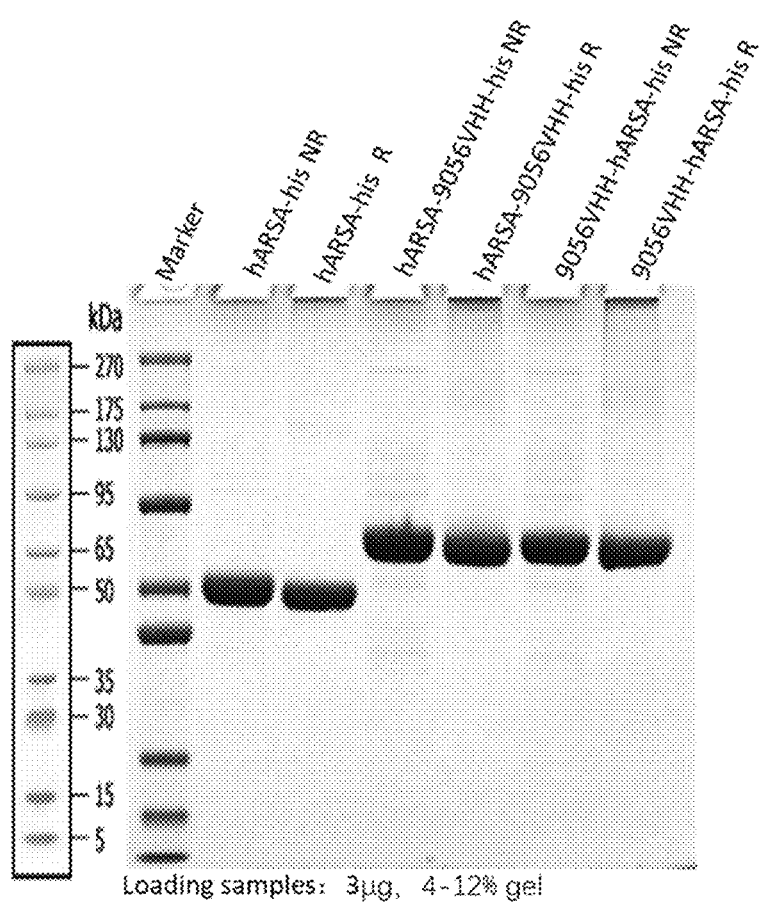
FIG. 2 shows the SDS-PAGE analysis of rhARSA recombinant proteins.

Example 2 Preparation of Recombinant Proteins 2.1 Protein Expression and Purification To produce 9056VHH-hARSA-his or hARSA-9056VHH-his proteins, a recombinant plasmid was constructed (hARSA has an amino acid sequence of SEQ ID NO: 10; 9056VHH comprises CDR1 having an amino acid sequence of SEQ ID NO: 1, CDR2 having an amino acid sequence of SEQ ID NO: 2, CDR3 having an amino acid sequence of SEQ ID NO: 3 and VHH having an amino acid sequence of SEQ ID NO: 8; the linker has an amino acid sequence of SEQ ID NO: 9). After confirming the sequence of the recombinant plasmid by sequencing, it was used as the vector for transient transfection of HEK293F cells, using lipofectamine or PEI as the transfection reagent, to produce the recombinant proteins in bulk. The cells were cultured in a shake flask with amount of 30 mL to 100 mL culture medium for 5-7 days. After centrifugation, the supernatant was purified using Ni-NTA agarose. The purified proteins were analyzed in non-reducing (NR) or reducing (R) conditions on a 4-12% gradient SDS-PAGE gel (FIG. 2).

Figure 3A:
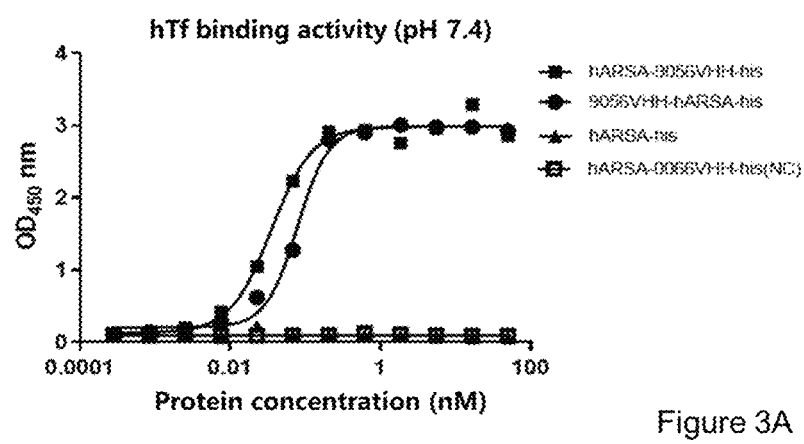
FIGS. 3A and 3B show the binding ability of rhARSA recombinant proteins with human transferrin (hTf).
Figure 3B:
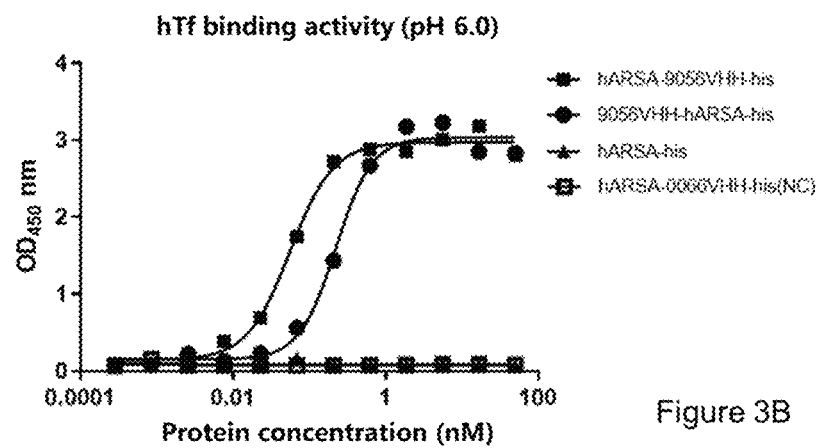

Example 3 Biological Properties of Recombinant Proteins 3.1 Binding Ability of Recombinant Proteins to Transferrin by ELISA A 96-well plate was coated with streptavidin (0.1 μg/mL, 100 μL/well) and incubated overnight at 4° C.; after washing the plate three times with buffer PBST, the 96-well plate was blocked with 200 μL of PBST containing 1% bovine serum albumin (BSA) for 1 hour at room temperature. The plate was then washed three times with PBST, added with biotinylated human transferrin (1 μg/mL, 100 μL/well) and incubated at room temperature for 1 hour. The plate was then washed three times with PBST, added with series dilutions of hARSA or hARSA-9056VHH proteins and incubated at room temperature for 1 hour. The plate was then washed three times with PBST, added with goat anti-hARSA antibody (R&D, AF2485) (100 μL/well) at a concentration of 0.125 μg/mL to each well and incubated at room temperature for 1 hour. The plate was then washed three times with PBST, added with 100 μL anti-goat IgG-HRP to each well and incubated at room temperature for 0.5 hour, followed by the same washing steps aforementioned. The plate was then added with 100 μL/well of TMB substrate solution and incubated at room temperature for 15 minutes. The reaction was then stopped by adding 100 μL/well of the stop solution, and the absorbance was read at 450 nm using an ELISA reader. The results, as shown in FIGS. 3A-3B, indicate that hARSA-9056VHH can bind to human transferrin, while hARSA cannot bind to human transferrin.

3.2 FACS Assay for Recombinant Proteins

Figure 4:
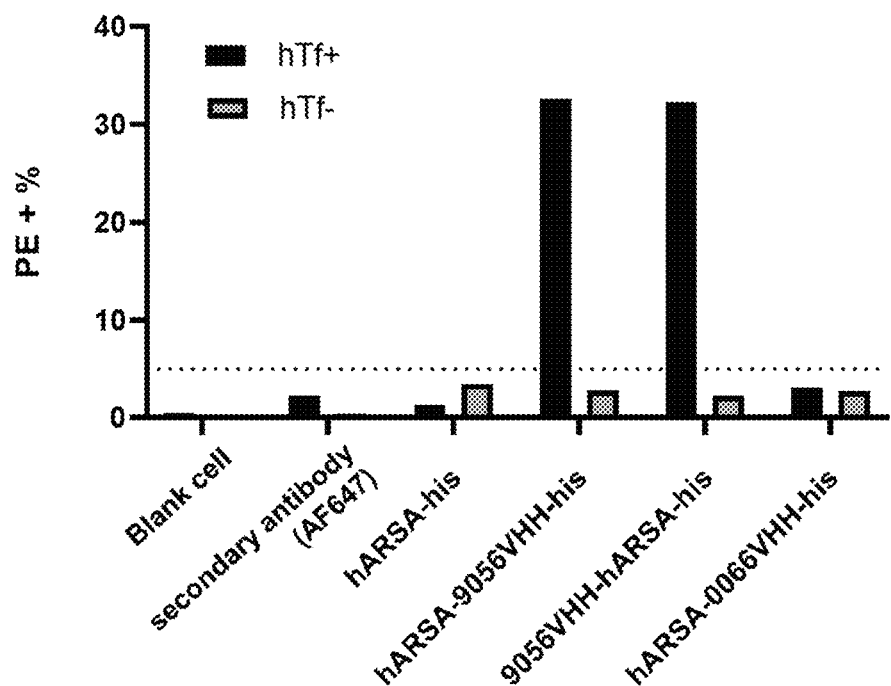
FIG. 4 shows the FACS result of the binding between rhARSA recombinant proteins and hTf/hTfR1.

A 293F cell line stably expressing human transferrin receptor 1 (hTfR1, UniProt P02786) was used to detect the binding of recombinant proteins to transferrin and to assess whether said binding disturbs the interaction between the transferrin and transferrin receptor on the cell membrane surface. 293F/hTfR1 cells were seeded into a 96-well plate at a density of $0.5 \times 10^6$ cells per well, and the plate was centrifuged at 4° C., 1000 rpm for 5 minutes. After washing with 200 μL of 1×PBS (pH 7.4), the cells were resuspended, blocked with 200 μL of PBS containing 2% BSA (blocking buffer) and incubated at 4° C. for 30 minutes, followed by the same washing steps aforementioned. The cells were then resuspended in the blocking buffer containing a series of dilutions of recombinant proteins, with or without native human transferrin (Sigma, Cat NO. T3309). The cells were then incubated at 4° C. for 30 minutes, sequentially added with mouse anti-VHH antibody (Genscript) and goat anti-mouse IgG antibody labeled with AF647 (Abcam, CAT#ab150115) and incubated at 4° C. for 30 minutes. The cells were then centrifuged, washed, and resuspended in the blocking buffer for analysis using a flow cytometer to assess the binding of cells to the recombinant proteins. The results, as shown in FIG. 4, indicate that hARSA-9056VHH recombinant proteins can bind to human transferrin (hTf) and does not affect the binding of the transferrin to the cell membrane surface transferrin receptor.

Figure 5A:
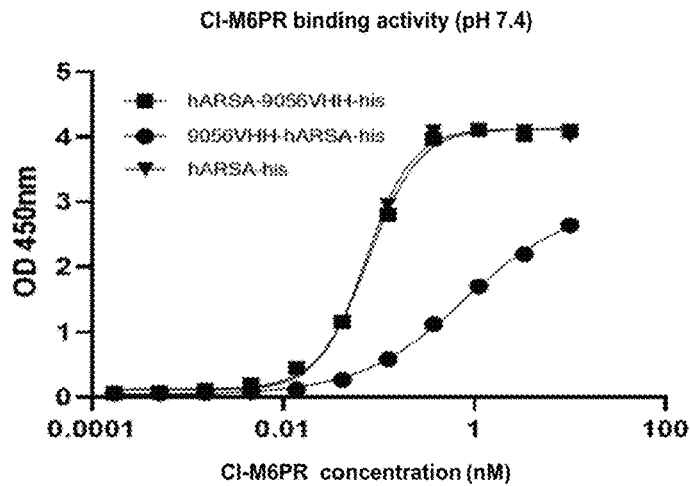
FIG. 5A shows that the fusion of hARSA protein with VHH does not affect the binding to M6PR.

3.3 Binding Ability of Recombinant 9056VHH-hARSA Proteins to M6P Receptor by ELISA A 96-well plate was coated by M6P receptor (M6PR-Fc comprising the extracellular domain of M6PR recombinantly expressed by HEK293F cells in house, 0.5 μg/well) and incubated overnight at 4° C. The plate was washed three times with PBST (phosphate-buffered saline, 0.1% Tween-20, pH 7.4) and blocked at room temperature for 1 hour by adding 200 μL of 1% BSA/PBST. The plate was then washed three times with PBST, added with a series of dilutions of rhARSA or rhARSA-9056VHH and incubated at room temperature for 1 hour. The plate was then washed three times with PBST, added with 0.125 μg/mL biotinylated goat Anti-hARSA antibody (R&D, BAF2485) (100 μL per well) to each well and incubated at room temperature for 1 hour. The plate was then washed three times with PBST, added with 100 µL of streptavidin-HRP (Sigma, CAT#S5512-1MG) to each well and incubated at room temperature for 1 hour. The plate was washed three times with PBST, added with 100 µL of TMB substrate solution and incubated at room temperature for 15 minutes. After the reaction was stopped, the absorbance at 450 nm was read using an enzyme-linked immunosorbent assay (ELISA) reader, and the data were analyzed using Graph Pad 8.0 software. The results, as shown in FIG. 5A, demonstrate that both rhARSA-9056VHH and rhARSA have similar binding abilities to the M6P receptor.

3.4 Uptake Recombinant Protein in mARSA$^{-/-}$ Mouse Skin Fibroblasts

The mARSA$^{-/-}$ mouse skin fibroblasts were isolated from C57BL/6J-Arsa$^{em1cyagen}$ (KOCMP-11883-Arsa-B6J) mice, which were purchased from Cyagen (Suzhou) Biotechnology Co., Ltd. The cells were cultured using high-glucose DMEM medium (containing 4.0 mM L-Glutamine, Sodium Pyruvate) (HyClone, SH30243.01) supplemented with 10% fetal bovine serum (FBS) (Gibco, 10099-141C). Once the cells migrated out and formed a confluent monolayer, they exhibited robust growth and were subsequently passaged for further experiments.

3.4.1 Dose-Dependent Cellular Uptake Assay

1) Well-growing P1 mARSA$^{-/-}$ mouse skin fibroblasts were seeded into a 96-well plate at a density of 2×10$^4$ cells per well and incubated overnight.

2) Solutions of 2-fold concentrations for 9056VHH-hARSA, hARSA (starting at 20 µM, 10-fold dilution) and 10 mM M6P (D-mannose-6-phosphate disodium salt hydrate (J & K, 530168)) were prepared; culture medium instead of M6P was used for the control group. The culture medium in the 96-well plate was discarded. The plate was added with 10 mM M6P, incubated for 15 minutes and then added with an equal volume of the corresponding protein solution (starting at 10 µM, 10-fold dilution) to each group, followed by incubation for 24 hours.

3) Collect cell lysates: 1×protease inhibitor was added and mixed well with the cell lysate for use. The medium was discarded and the cells was washed with PBS three times. The plate was added with 60 µL/well of cell lysate, and the lysate was collected in a 1.5 mL EP tube. The EP tube was then centrifuged at 12000 rpm. The supernatant was collected, measured for the total protein concentration, and stored at −80° C. for further analysis.

Figure 5B:
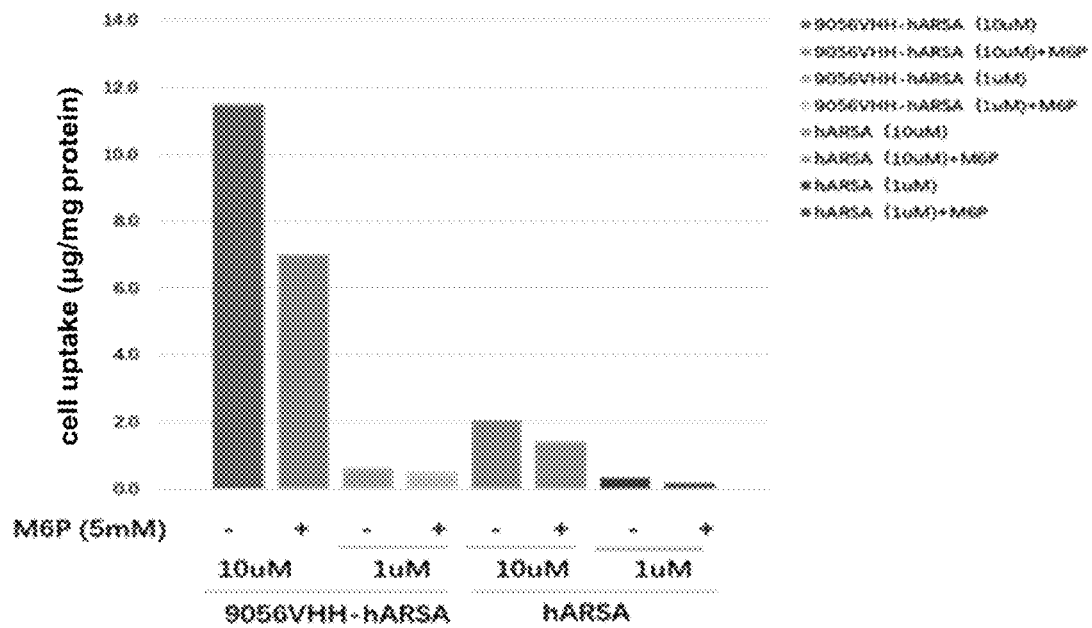
FIG. 5B shows that the uptake of 9056VHH-hARSA by mARSA$^{-/-}$ fibroblasts is 5.57 times that of hARSA (10 μM), partially blocked by M6P.

Protein concentration was detected by ELISA: a 96-well enzyme-linked plate was coated with goat Anti-hARSA antibody (R&D, AF2485) at 0.25 µg/mL. After washing three times with PBST (0.1% Tween-20), the plate was blocked with 200 µL of PBST containing 1% BSA at room temperature for 1 hour. After washing three times with PBST, the plate was added serially diluted detection samples (using serially diluted standard rhARSA and 9056VHH-rhARSA as the standard curve). The plate was incubated at room temperature for 1 hour, then washed three times with PBST, added with 0.125 µg/mL biotinylated goat Anti-hARSA antibody (R&D, BAF2485) and incubated at room temperature for 1 hour. After washing three times with PBST, the plate was added with Streptavidin-HRP (HRP) 1:5000 (Sigma, CAT#55512-1MG) and incubated at room temperature for 1 hour. After washing three times with PBST, the plate was added with 100 µL of TMB substrate solution, incubated for 15 minutes, and then the reaction was terminated. The plate was read for at 450 nm and calculated for the protein concentration based on the standard curve: cell uptake amount=protein concentration in the sample/total protein concentration. As shown in FIG. 5B, mARSA$^{-/-}$ fibroblasts uptake 9056VHH-hARSA at 5.57 times (10 µM) that of hARSA, and the uptake can be partially blocked by M6P.

3.4.2 Time-Dependent Cellular Uptake Assay

1) As in the experiment in section 3.4.1, a 20 µM protein solution was prepared and subsequently diluted 10 times to obtain a 2 µM solution (final concentration of 1 µM). The culture medium in the 96-well plate was discarded. The plate was added with 10 mM M6P and incubated for 15 minutes and then added with the corresponding protein solution to each group, followed by incubation for 48 hours, 24 hours, 6 hours, 2 hours, and 0 hours. The cell lysates were collected and centrifuged at 12,000 rpm. The supernatant was collected, measured for the total protein concentration and stored at −80° C. for further analysis.

Figure 5C:
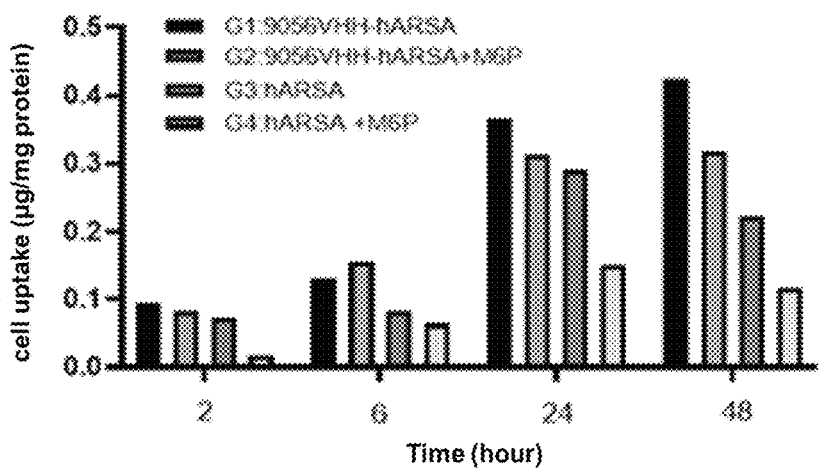
FIG. 5C shows the time-dependent uptake of 9056VHH-hARSA by fibroblast cells.

2) As in the experiment in section 3.4.1, ELISA was used to detect the protein concentration in the cell lysates. The cell uptake amount of the protein at each time point was calculated as follows: cell uptake amount=protein concentration in the sample/total protein concentration. As shown in FIG. 5C, mARSA$^{-/-}$ fibroblasts exhibit time-dependent uptake of 9056VHH-rhARSA.

3.5 Intracellular Localization of Recombinant Proteins Uptaken by mARSA−/− Mouse Skin Fibroblasts

3.5.1 Incubation

As in the experiment in section 3.4, mARSA$^{-/-}$ mouse skin fibroblasts were cultured. A 24-well plate with coverslip was seeded with cells growth well and cultured to 70-80% confluence. The medium was discarded, the plate was added with culture medium containing 2 µM 9056VHH-hARSA or hARSA, followed by incubation for another 24 hours.

3.5.2 Immunofluorescence Staining and Laser Confocal Microscopic Observation 1) Fixation: The culture medium was discarded and the cells were washed three times with ice-cold PBS and then fixed with 4% paraformaldehyde in PBS pH 7.4 at room temperature for 10 minutes, followed by washing three times with ice-cold PBS.

2) Permeabilization: The samples were incubated with 0.1% Triton X-100 in PBS at room temperature for 10 minutes. The cells were washed three times with ice-cold PBS.

3) Blocking: The cells were blocked with 1% BSA in PBST (PBS+0.05% Tween 20) for 30 minutes and washed three times with ice-cold PBS.

4) Immunofluorescence staining: The cells were incubated with primary goat anti-human ARSA antibody (R&D, AF2486) diluted 1:100 in 1% BSA PBST at room temperature for 1 hour and washed three times with ice-cold PBS. The cells were then incubated with PE-conjugated secondary donkey anti-goat IgG antibody (R&D, F0107) and lysosome specific CD107a (LAMP-1) antibody (eBio1D4B (1D4B)) (Alexa Fluor 488, eBioscience™, 53-1071-82) at room temperature in dark for 1 hour and washed three times with ice-cold PBS.

5) Mounting: The cells were mounted with ProLong® Gold Antifade Reagent with DAPI (CST, #8961) and stored at 4° C. in dark. The cells were observed and imaged using a laser confocal microscope.

Figures 6A, 6B, 6C:
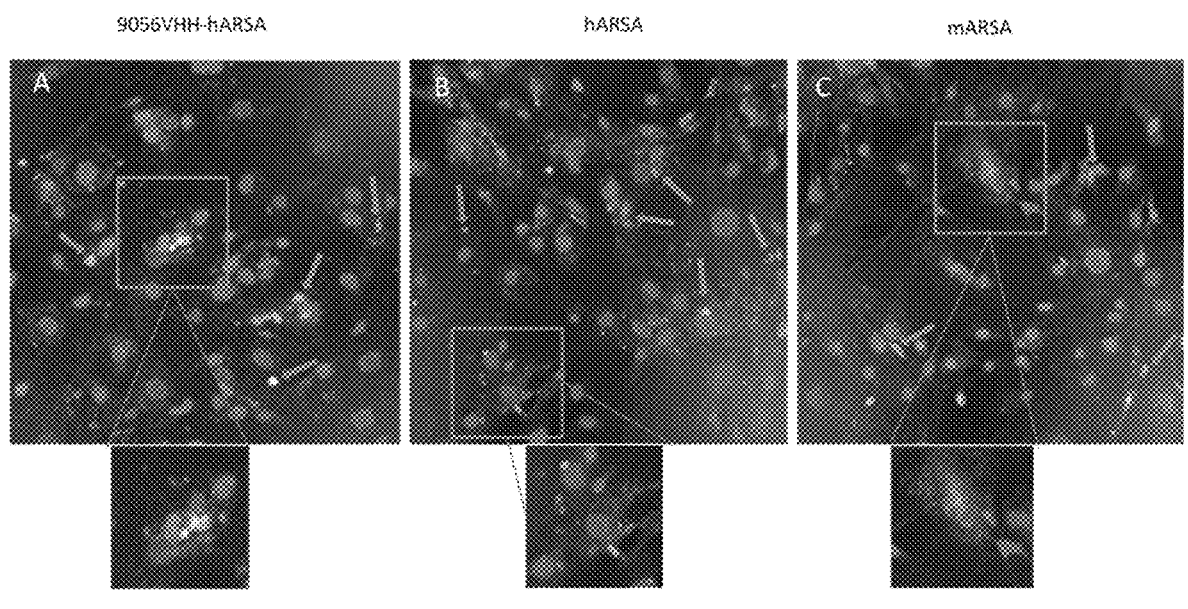
FIGS. 6A-6C show the intracellular localization of ARSA recombinant proteins in mARSA$^{-/-}$ fibroblasts after uptake observed using Laser scanning confocal microscope (LSCM).

As shown in FIGS. 6A-6C, a large amount of 9056VHH-hARSA (FIG. 6A) and hARSA (FIG. 6B) recombinant proteins can be internalized by mARSA$^{-/-}$ mouse skin fibroblasts and transported to lysosomes (indicated by arrows).

Example 4 Biological Activity Assay of Recombinant Proteins 4.1 In Vitro Enzyme Activity Assay (pNCs Artificial Substrates)

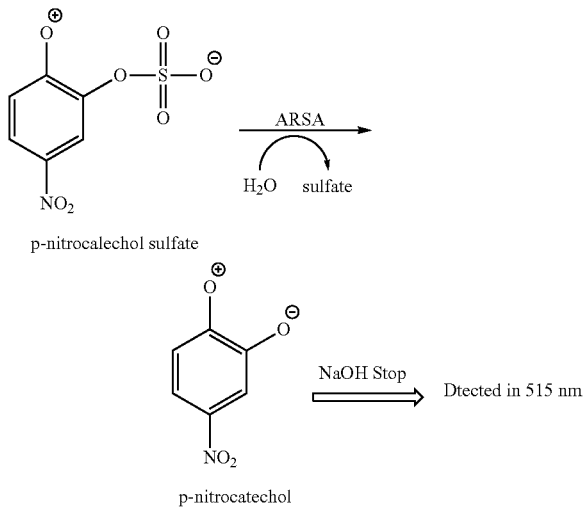

Preparation of Solutions 1) p-nitrocatechol (pNC, TCI, Lot # N5V4L-RT) standard solution: 1 mM pNC was dissolved in the termination solution (MW=155.11, 5 mg in 32.23 mL).
2) Termination solution: 0.8 g NaOH was dissolved in 100 mL water for the preparation of 0.2 M NaOH (MW=40).
3) Assay Buffer (Reaction buffer): A solution was prepared to contain 50 mM sodium acetate (NaOAc), 0.5 M sodium chloride (NaCl), and the pH of the solution was adjusted to 4.5 using acetic acid (HOAc).
4) p-nitrocatechol sulfate (pNCS, sigma, Lot # MKCN3971) stock solution: 2 mM pNCS was dissolved in the assay buffer (MW=311.35, 10 mg in 16 mL).

Procedures 1) pNC standard curve: 0, 20, 40, 60, 80, 100 µL of pNC standard solution was added to a 96-well plate. The total volume in each well was adjusted to 100 µL per well using the stop solution. The corresponding pNC concentrations in each well were 0, 20, 40, 60, 80, and 100 nmol/well, respectively.
2) rhARSA or 9056VHH-hARSA was diluted with assay buffer to 200 nM (final concentration is 100 nM) with or without hTf.
3) pNCS was diluted to 2 mM with assay buffer (final concentration is 1 mM).
4) 75 µL of 200 nM rhARSA or 9056VHH-hARSA was mixed with 75 µL of 2 mM pNCS. For a blank control, 75 µL of assay buffer was mixed with 75 µL of substrate mixture. The plates were incubated at 37° C. for 0, 5 minutes, 10 minutes, 15 minutes, and 30 minutes, respectively.
5) 150 µL of 0.2 M NaOH was added to stop the reactions.
6) 200 µL of each reaction solution was transferred to a new 96-well plate, and then measured at 515 nm using a microplate reader.
7) Based on the standard curve, the enzyme activity-time curve was plotted and the specific enzyme activity was calculated.

Figure 7A:
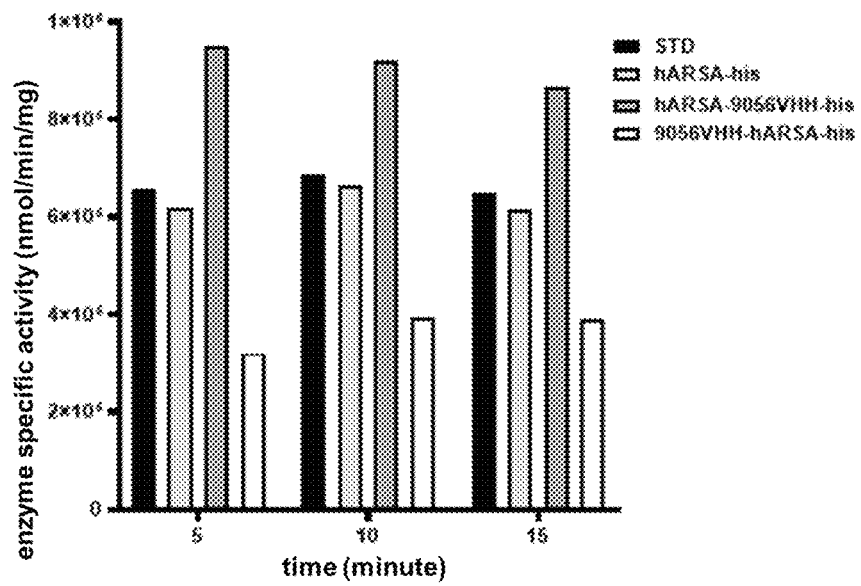
FIG. 7A and FIG. 7B show the in vitro enzyme specific activity of ARSA recombinant proteins (substrate: pNCS).
Figure 7B:
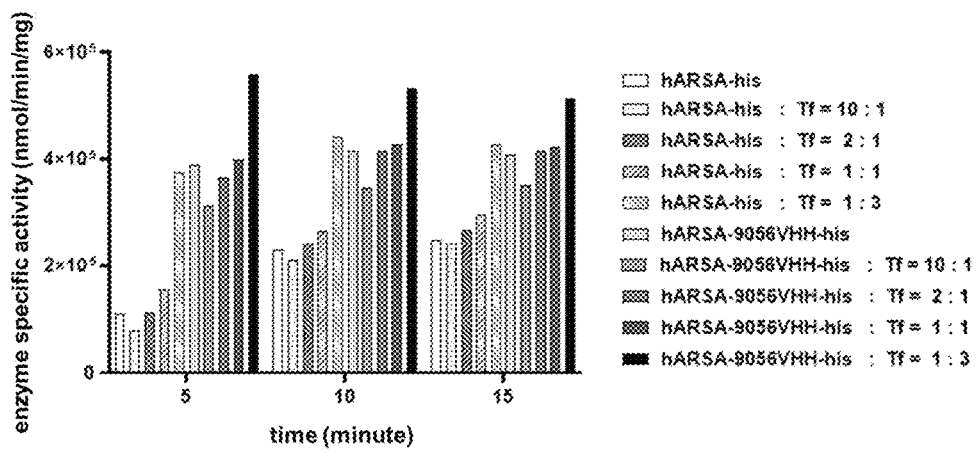

The results, as shown in FIG. 7A, indicate that the recombinant enzyme proteins produced in the CHO K1 maintain good enzyme activity (FIG. 7A). Additionally, the binding of the recombinant enzyme to human transferrin does not affect its enzyme activity (FIG. 7B).

Figure 8:
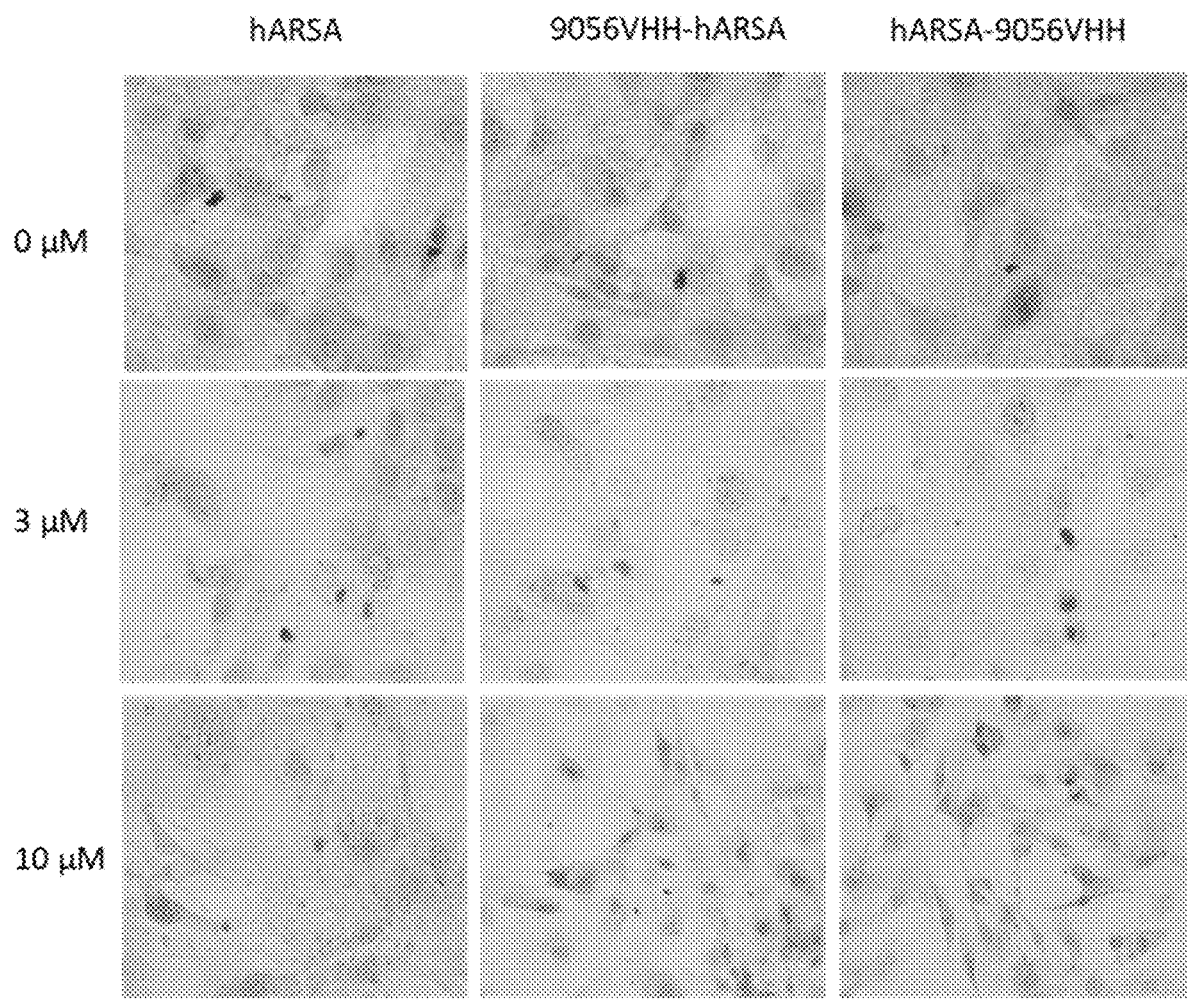
FIG. 8 shows the sulfatide reduction in mARSA$^{-/-}$ fibroblasts treated with hARSA, 9056VHH-hARSA, and hARSA-9056VHH (10 μM, 3 μM, 0 μM) for 48 hours with Alcian Blue/Fast red staining.

4.2 Recombinant Proteins Reduced Sulfatide Deposition in mARSA-/- Mouse Skin Fibroblasts in Vitro As in the experiment in section 3.4, mARSA$^{-/-}$ mouse skin fibroblasts were seeded in a 24-well plate and cultured until 80-90% confluence. The cells were then treated with different concentrations of 9056VHH-hARSA: 10 µM, 3 µM, and 0 µM, for 48 hours. After discarding the medium, the cells were stained by Alcian blue (ABS)-fast red staining kit (pH 1.0) according to the manufacturer's instructions (Beyotime Biotechnology, Catalog No. C0153S). The staining was carried out at room temperature for 1 hour. After staining, the cells were washed three times with distilled water and then counterstained with fast red for 5 minutes, washed with water and observed under a microscope. The results, as shown in FIG. 8, indicate that mARSA$^{-/-}$ fibroblasts treated with 10 µM, 3 µM, and 0 µM 9056VHH-hARSA for 48 hours exhibited blue spots or patches in the cytoplasm. The blue staining demonstrates the presence of sulfuric acid esters, which are metabolites of sulfate ions. ABS staining was used to detect sulfatide substrate in cells. Sulfatide deposition showed as dark blue spots or patches in cytoplasm. There was no obvious blue spots or patches in 10 µM 9056VHH-hARSA treated cells. While much more and bigger sulfatide depositions were observed in 0 and 3 µM 9056VHH-hARSA treated cells. These results elucidated the mechanism of action of 9056VHH-hARSA in vitro. 9056VHH-hARSA can be endocytosed into the cells, enter the lysosome, and play a role in degrading the sulfatide deposition.

Example 5 In Vitro Plasma Stability Assay 5.1 Mouse Plasma Stability Assay

Figure 9A:
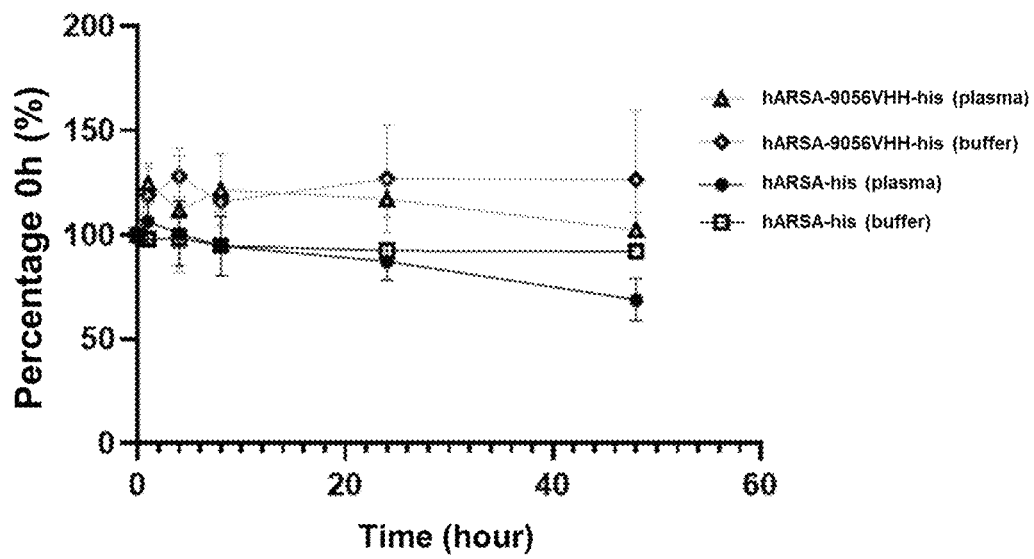
FIG. 9A and FIG. 9B show the results of in vitro plasma stability of ARSA recombinant proteins.

1) Sample preparation: Standard protein samples were prepared in mouse plasma at a concentration of 6 µg/mL. The samples were then incubated at 37° C. under constant humidity for 1 hour, 4 hours, 8 hours, 24 hours, and 48 hours. After the incubation, the samples were rapidly frozen in liquid nitrogen and stored at −80° C. for further use. Protein samples without plasma were used as positive controls.
2) ELISA assay: SLN7134 (anti-9056VHH, custom-made by Linno Pharmaceuticals) at a concentration of 1 µg/mL was coated onto a 96-well plate (100 μL per well) and incubated overnight at 4° C. The plate was then blocked with 1% BSA TBST (200 μL per well) at 37° C. for 1 hour. A standard curve was prepared by diluting the protein in 1% BSA TBST, starting at a concentration of 200 ng/mL and creating a two-fold serial dilution, 100 μL per well, incubated at room temperature for 1 hour. The plasma samples were diluted to an appropriate concentration range (100-fold, 200-fold, and 300-fold) with 1% BSA TBST and incubated in each well at room temperature for 1 hour. SLN7165-Biotin (biotinylated anti-human ARSA antibody, custom-made by Linno Pharmaceuticals) was diluted in 1% BSA TBST to a final concentration of 0.5 μg/mL and added to each well (100 μL per well), followed by incubation at room temperature for 1 hour. SA-HRP (Sigma, CAT#S5512-1MG) was diluted 1:5000 in 1% BSA TBST and added to each well (100 μL per well), followed by incubation at room temperature for 0.5 hours. Chromogenic reacted with 100 μL of TMB and stopped by 100 μL of stop solution. The absorbance at 450 nm was measured using a microplate reader, and the data were analyzed with GraphPAD 8.0. The results, as shown in FIG. 9A, demonstrate that rhARSA-9056VHH-his (the tested protein) exhibits good stability in mouse plasma.

5.2 Human Plasma Stability Assay

Figure 9B:
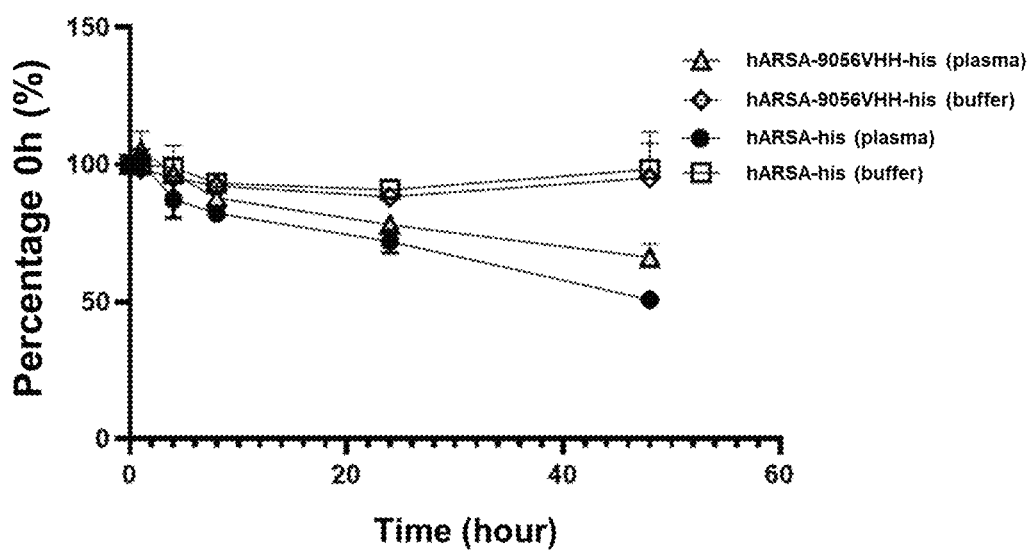

The recombinant protein incubated in human plasma at 37° C. for indicated time and the concentration was measured using the ELISA method in the same protocol and/or methods as described in 5.1. The results are shown in FIG. 9B: rhARSA-9056VHH-his is stable in human plasma.

Figure 10:
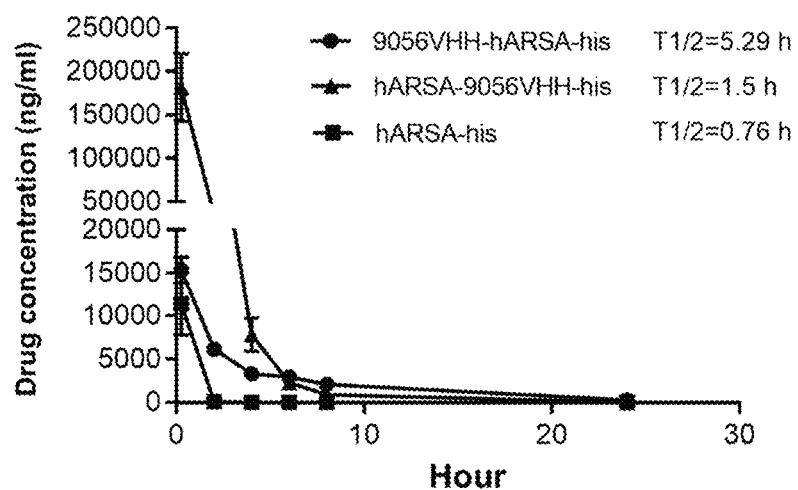
FIG. 10 shows the half-life of hARSA, hARSA-9056VHH and 9056VHH-hARSA in mouse blood.

Example 6 Pharmacokinetic (PK) Studies of Recombinant Proteins in Mice 6.1 PK Assay Development A 96-well ELISA plate was coated with goat Anti-hARSA antibody (R&D, AF2485), washed 3 times with PBST (Tween-20, 0.1%) and then blocked with 200 μL of 1% BSA PBST at room temperature for 1 hour. After washing three times with PBST, the plate was added with 100 μL/well of a sample containing 1% mouse serum (used as the sample matrix) and a serially diluted standard (rhARSA or rhARSA-9056VHH). After incubation at room temperature for 1 hour, the plate was washed 3 times with PBST, added with biotin-labeled goat Anti-hARSA antibody (R&D, BAF2485) and incubated at room temperature for 1 hour. After washing three times with PBST, the plate was added with Streptavidin-labeled horseradish peroxidase (HRP) (Sigma, CAT#S5512-1MG) and incubated at room temperature for 30 minutes. After washing three times with PBST, the plate was incubated with 100 μL of TMB for 15 mins, and stopped with a stop solution. The absorbance at 450 nm was read. FIG. 10 shows the results of the validation of the PK method with three standard concentrations (high, medium, and low), which indicates that the precision (CV %<20%) and accuracy (RE %+/−25%) of this method meet the requirements of the samples to be assayed.

6.2 Single-Dose PK Studies

PK studies were performed in 6-8 weeks old male C57BL/6 mice. The animals were grouped according to their body weight and were supplied intraperitoneally with 10 mg/kg of human transferrin on the day prior to the administration of the drug and daily during the study period. A single dose of 3 MPK rhARSA, rhARSA-9056VHH and 9056VHH-rhARSA was intravenously administered by tail vein. Blood samples were collected after 2, 4, 8, 24 and 48 hours, respectively. Samples were quantified by ELISA assay described in 6.1 and the PK profiles were calculated by PK sovler software. The results shown in FIG. 10 indicate that at 3 MPK dose, there is a significant increased of rhARSA-9056VHH blood half-life (5.29 hours) and 9056VHH-rhARSA blood half-life (1.50 hours) as compared to rhARSA blood half-life (less than 0.76 hour). The blood half-life of rhARSA is significantly prolonged by 9056VHH binding with human transferrin.

6.3 Single-Dose PK Studies of Crossing the Blood-Brain Barrier

Figure 11A:
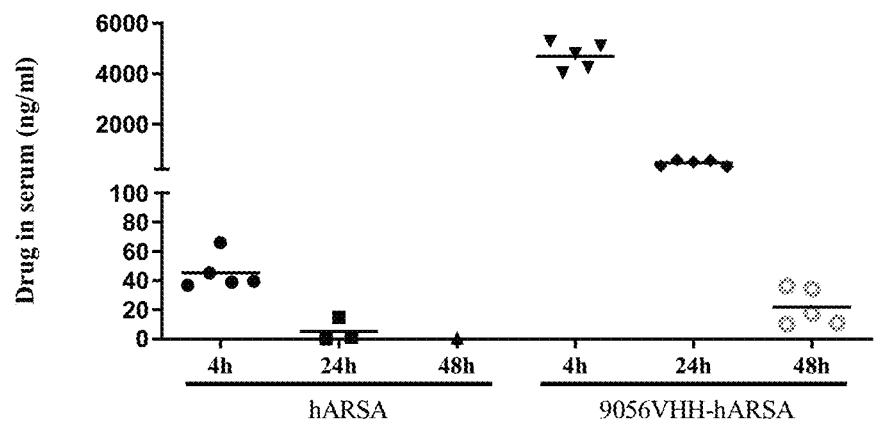
FIG. 11A and FIG. 11B show the efficiency of hARSA and 9056VHH-ARSA in crossing the BBB in wild-type C57bl/6 mice.
Figure 11B:
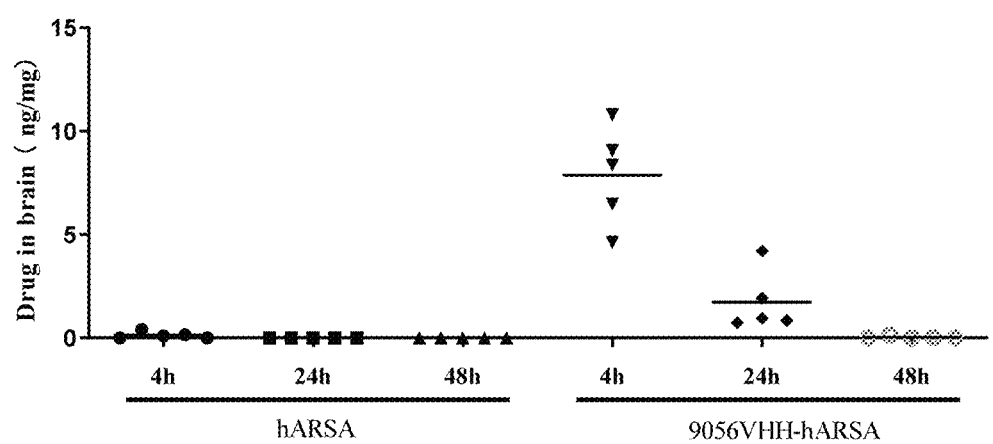

PK studies were performed in 6-8 weeks old male C57BL/6 mice. The animals were grouped according to their body weight and were supplied intraperitoneally with 10 mg/Kg of human transferrin on the day prior to drug administration and daily during the study period. The hARSA or 9056VHH-hARSA was intravenously administered by tail vein at a dose of 10 MPK. Blood samples and cerebrospinal fluid were collected at 4, 24, and 48 hours after drug administration, respectively; and brain tissues were collected after perfusion with 20 mL PBS. The drug concentration (i.e., the concentration of hARSA or 9056VHH-hARSA) in serum, cerebrospinal fluid and brain tissue homogenate were detected by the method described in 6.1. Graph Pad 8.0 software was used to analyze the data and calculate the efficiency of crossing the blood-brain barrier (ID % (injected dose)=brain tissue drug concentration (ng/mg tissue)/10 mg/kg×100%). The results were shown in FIGS. 11A-11B. FIG. 11A shows that the average blood drug concentration of hARSA is about 45 ng/mL (4 hours), and undetectable at other time points. The blood drug concentration of 9056VHH-hARSA is about 5000 ng/mL (4 hours), ~400 ng/mL (24 hours), and ~18 ng/mL (48 hours), respectively, which is significantly higher than that of the hARSA group. FIG. 11B shows that hARSA-his is undetectable in any of the brain tissue homogenates at indicated time points, while the concentrations of 9056VHH-hARSA in brain tissue homogenates was 4.6~10.8 ng/mg brain tissue (4 hours), 0.7~4.2 ng/mg brain tissue (24 hours), and the efficiency of crossing the blood-brain barrier is much higher than that of the hARSA group.

6.4 Single Ascending Dose PK Studies of Crossing the Blood-Brain Barrier

Figure 12A:
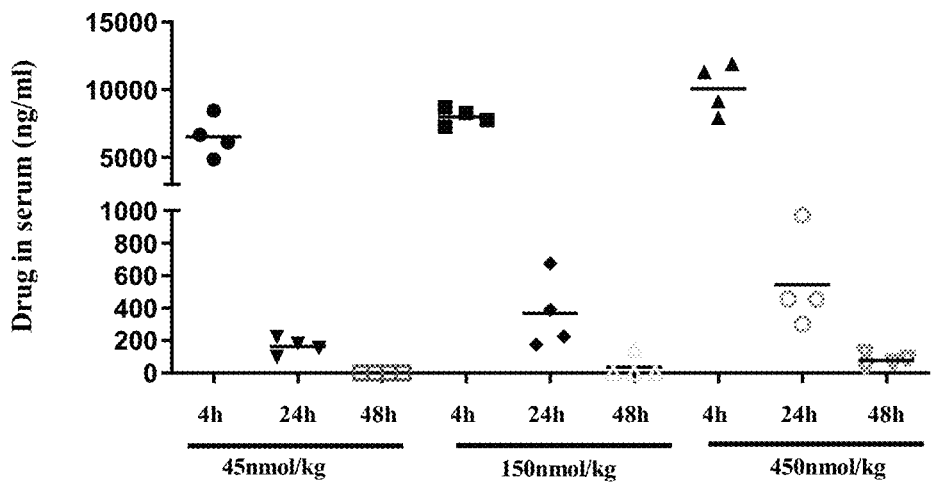
FIG. 12A, FIG. 12B and FIG. 12C show the efficiency of 9056VHH-ARSA (in ascending doses) in crossing the BBB in wild-type C57bl/6 mice.
Figure 12B:
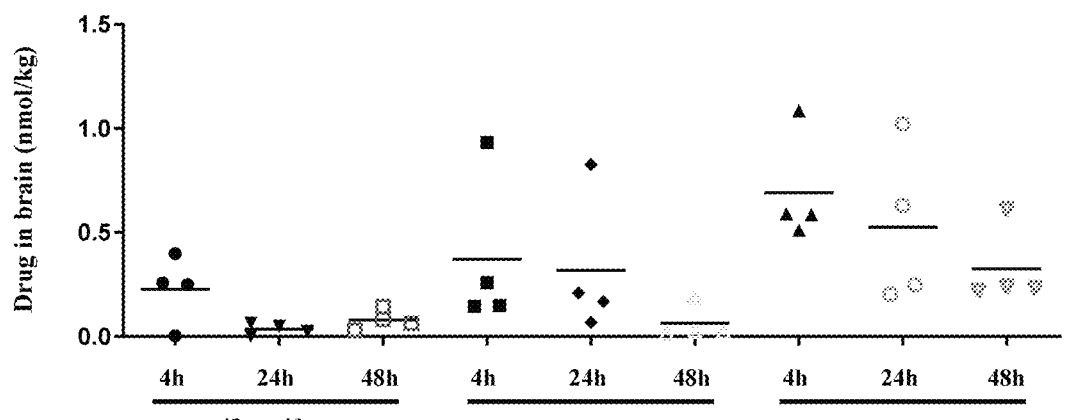
Figure 12C:
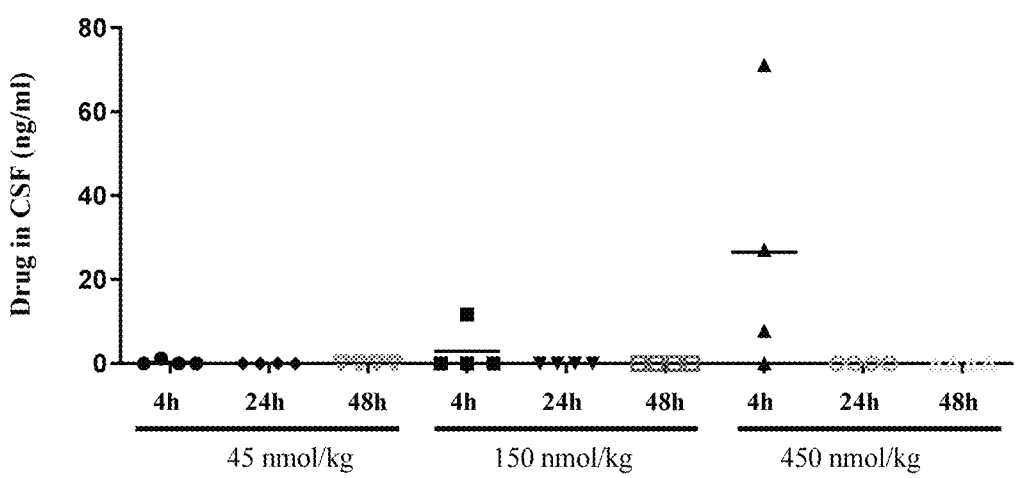

Same as in the experimental method in the section 6.3, 45 nmol/kg, 150 nmol/kg, and 450 nmol/kg of 9056VHH-hARSA were intravenously injected by tail vein. The drug concentration (i.e., the concentration of 9056VHH-hARSA) in serum, cerebrospinal fluid, and brain tissue homogenate were measured by the method described in 6.1, respectively. The data were analyzed by the Graph Pad 8.0 software, and the efficiency of crossing the blood-brain barrier was calculated (% ID (injected dose)=brain tissue drug concentration (nmol/mg tissue)/injected dose (nmol/kg)×100%). The results are shown in FIGS. 12A-12C. FIG. 12A shows blood concentrations of 9056VHH-hARSA at 4, 24, and 48 hours after administration, respectively. FIG. 12B shows 9056VHH-hARSA concentration in brain homogenates at 4, 24, and 48 hours after administration. The average injected dose percentage (% ID) for each group (45 nmol/kg-4 h (3 MPK); 150 nmol/kg-4 h (10 MPK); 450 nmol/kg-4 h (30 MPK)) is 0.503%, 0.25%, and 0.15%, respectively. FIG. 12C shows that 9056VHH-hARSA is lower in CSF.

Figure 13A:
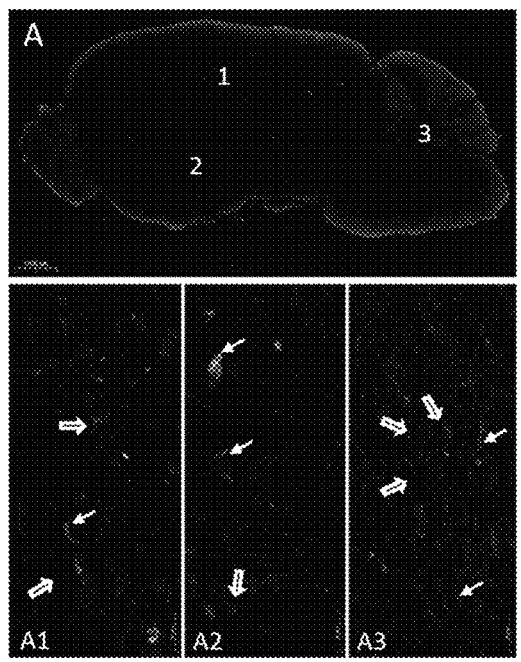
FIGS. 13A and 13B show the distribution and organelle localization of hARSA-9056VHH in MLD model mice after intravenous injection at 30 MPK for 2 hours.
Figure 13B:
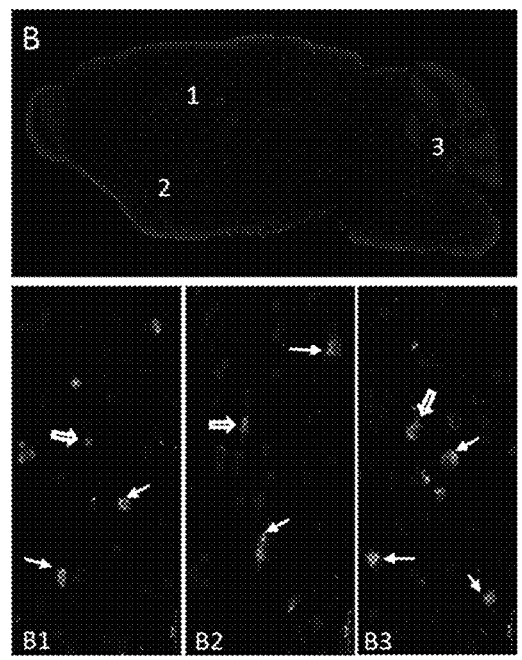

6.5 Drug Distribution in Brain Tissue after a Single Dose Administration of rhARSA-9056VHH in MLD Mice Same as described in the section 6.3, rhARSA-9056VHH was intravenously administered by tail vein at a dose of 150 nmol/kg or 450 nmol/kg. 2 hours after administration, mice were euthanized, brain tissue was collected and fixed in 4% paraformaldehyde. Paraffin sections of brain tissue were prepared, 5 μm sagittal cut (by Shanghai Ribiology Co., Ltd.). hARSA/CD31/Lamp1 immunofluorescence co-staining were performed. Slides were co-incubated with primary antibody, goat anti-human ARSA antibody (R & D, AF2486) or rabbit anti-mouse CD31 antibody (Abcam, ab281583), diluted with 1% BSA PBST 1:100 for 1 hour at room temperature, and then washed with pre-cooled PBS for 3 times. The slides were then co-incubated with PE-labeled secondary antibody, donkey anti-goat IgG antibody (R&D, F0107), and CD107a (LAMP-1) (eBio1D4B (1D4B)) (Alexa Fluor 488, eBioscience™, 53-1071-82) for 1 hour at room temperature in dark. The slides were mounted with ProLong® Gold Antifade Reagent with DAPI (CST, #8961), stored at 4° C. in dark, and observed and photographed with laser confocal microscopy. The results are shown in FIGS. 13A-13B. FIG. 13A: the drug (rhARSA-9056VHH) can cross the blood-brain barrier to enter the brain tissue (anti-hARSA), and vascular endothelial cells (anti-CD31). The drug is also in the vascular endothelial cells. FIG. 13B: the drug that enters into the brain cells (anti-hARSA) is co-localized with the lysosomal membrane protein (anti-Lamp1).

6.6 PET/CT Imagine Study in Cynomolgus Monkeys

6.6.1 Animals and Sample Collection

One non-naïve cynomolgus monkey (male) in each group was infused intravenously with 10 MPK or 30 MPK $^{124}$I-rhARSA-9056VHH, and PET/CT dynamic scanning of the brain was started immediately for 2 hours (0-2 hours), followed by PET/CT static scanning at 7 selected time points: 6 h, 10 h, 24 h, 48 h, 72 h, 96 h, and 144 h after administration.

Figure 14A:
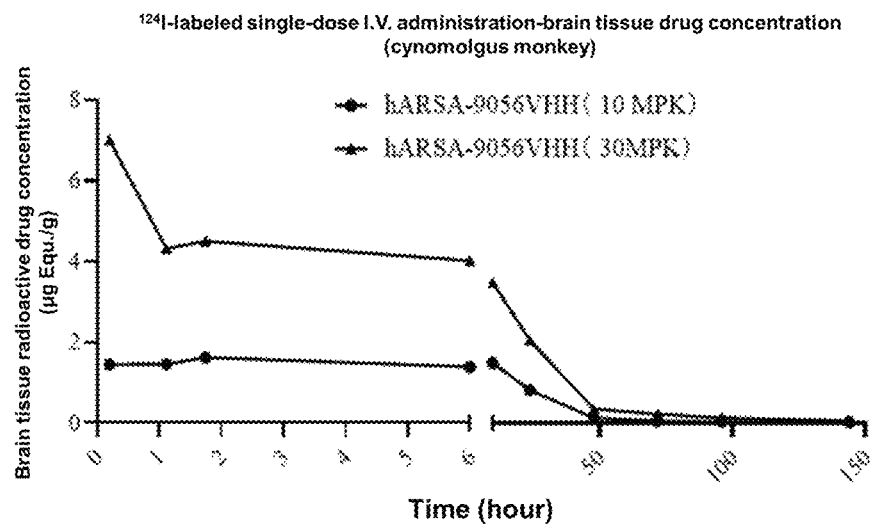
FIG. 14A, FIG. 14B and FIG. 14C show the PK study results of recombinant hARSA-9056VHH crossing the BBB in cynomolgus monkeys.
Figure 14B:
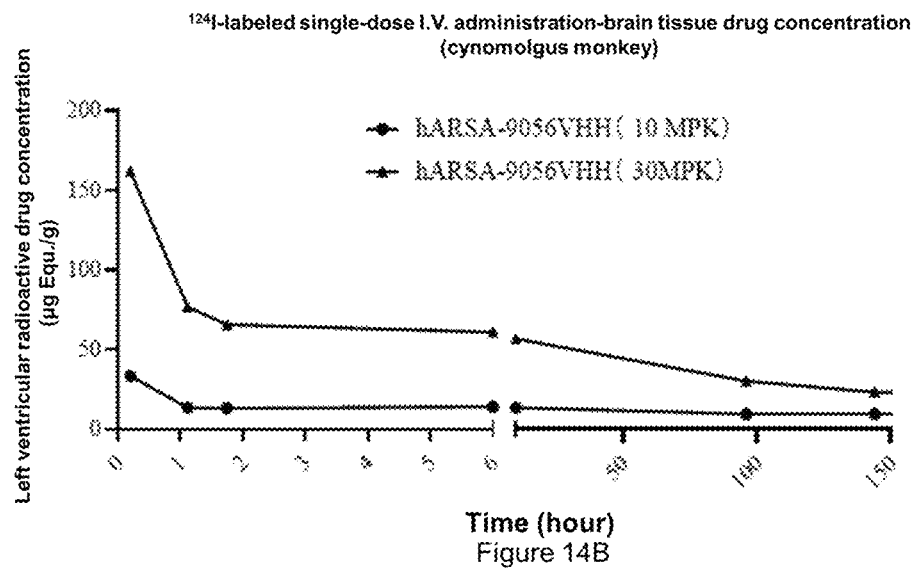
Figure 14C:
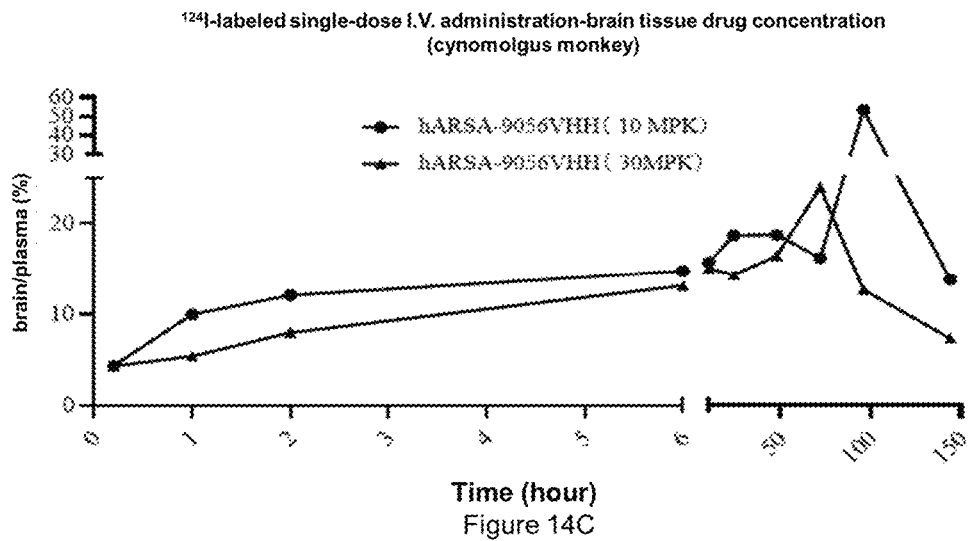

6.6.2 Data Analysis $^{124}$I-rhARSA-9056VHH brain penetration efficiency (Kp=brain (radiation dose)/blood (radiation dose) ratio was calculated. The results are shown in FIGS. 14A-14C. FIG. 14A shows brain tissue drug concentration-time curve. FIG. 14B shows left ventricular drug concentration-time curve. FIG. 14C shows percentage drug concentration of brain tissue to left ventricular. Twenty to thirty minutes after the administration, there is a significant increased brain/plasma ratio, which indicates that hARSA-9056VHH can be accumulated and retained in the brain tissue. Brain/plasma ratio reached the peak at 96 h (53.3%) in 10 MPK group. Brain/plasma ratio reaches the peak at 72 h (23.95%) in 30 MPK group.

Example 7 Pharmacodynamic Study in the mARSA-Deficient Mouse Model of MLD

7.1 mARSA-Deficient Mice

The mARSA gene (GenBank: Gene ID 11883)-deficient mice were genotyped as C57BL/6J-Arsa$^{em1cyagen}$ (KOCMP-11883-Arsa-B6J), verified by PCR and sequencing.

7.2 In Vivo Pharmacodynamic Studies of rhARSA-9056VHH

7.2.1 Animals

Ten to twelve months old and healthy homozygote mARSA$^{-/-}$ mice were selected. Matched by sex and age. Mice were weighed and recorded, numbered and cage card information was filled in. hTf (10 mg/kg) was injected intraperitoneally once daily to supply hTf in the mice.

7.2.2 Drug Delivery

Drug: hARSA-9056VHH. Frequency of administration: BIW×4 or BIW×8. Dosages: 10 MPK or 30 MPK. The day before administration, the drug was premixed with hTf at a molar ratio of 1:1 overnight at 4° C. The mice were weighed in the morning of the day of administration, and the volume of drug to be administrated was calculated accordingly. The drug was intravenously administered by tail vein. The time of administration was recorded.

Daily records: the weight of the mice was weighed and recorded, the status and activity level, etc. of the mice was observed and recorded.

7.2.3 Behavioral Assessment in Mice: the Balance Beam Test

1) Training period: On the first day, a balance beam was used, and the mice were trained to enter a small dark box through the square balance beam. Each mouse was trained 3 times. On day 2, the same as on day 1 were repeated.

2) Test period: On the third day, mice passed through the square balance beam into the small dark box. The whole process was videotaped and the time of passing through the balance beam was recorded.

Figure 15:
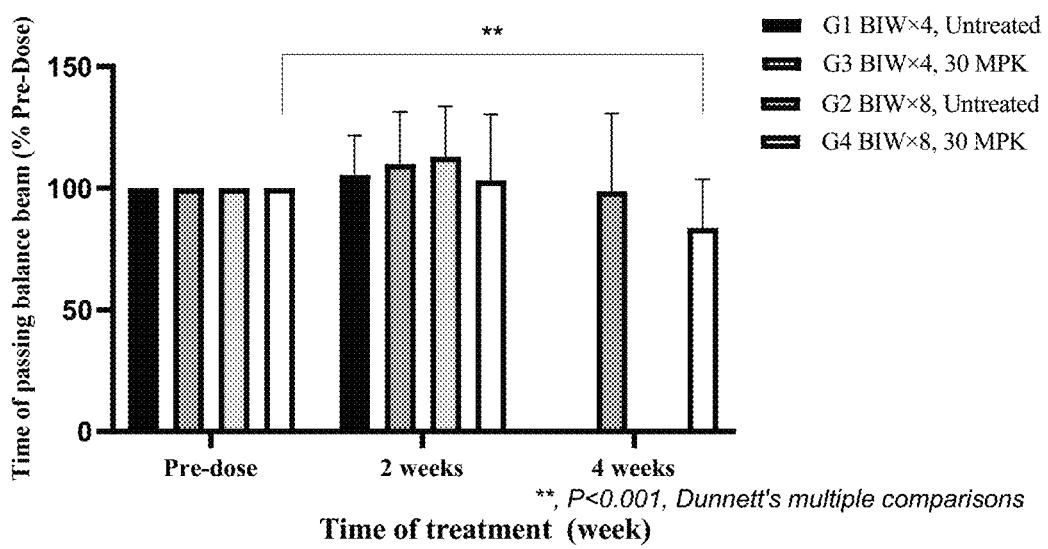
FIG. 15 shows the assessment of motor function in mARSA-deficient mice after treatment with hARSA-9056VHH.
Figure 16A:
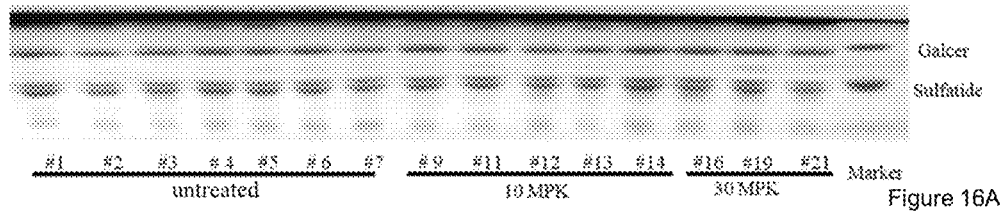
FIGS. 16A-16F show the TLC detection of cerebroside sulfate substrate levels in brain tissue of mARSA-deficient mice after treatment with hARSA-9056VHH.
Figure 16C:
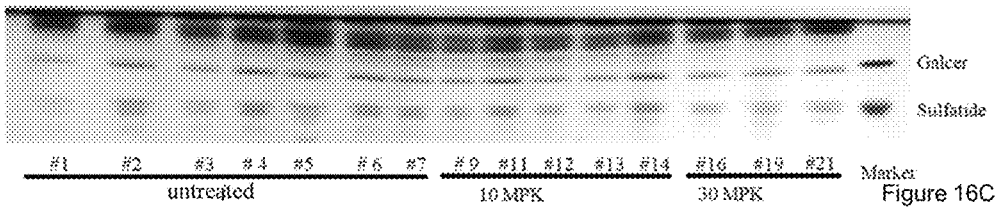
Figure 16E:
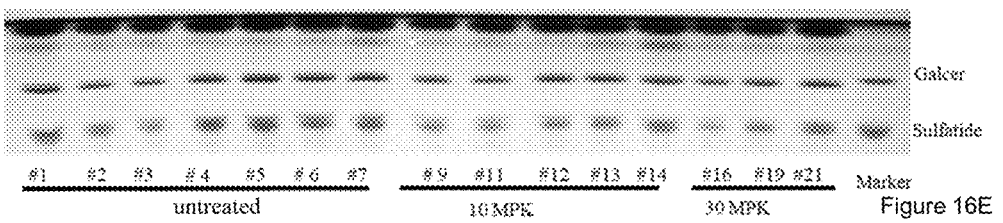
Figure 16B:
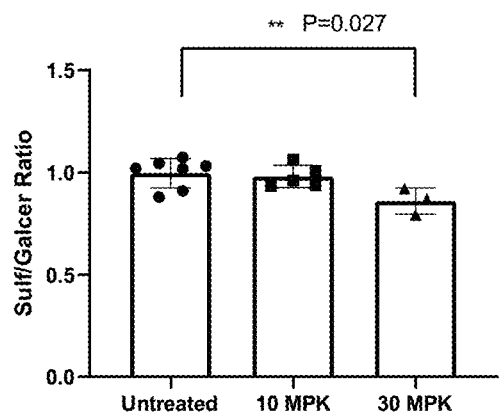
Figure 16D:
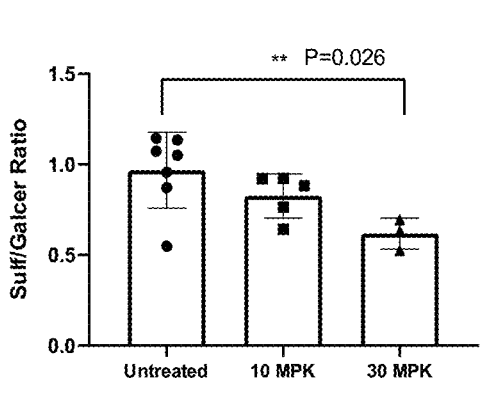
Figure 16F:
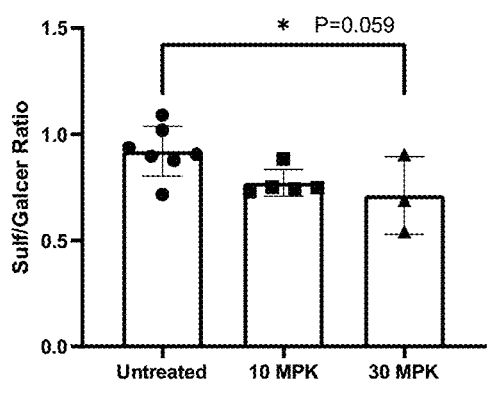
Figures 17A, 17B, 17C:
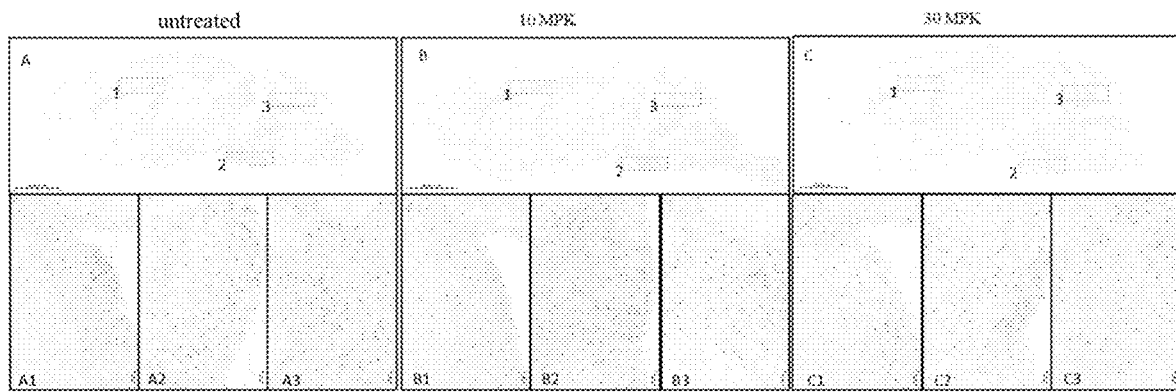
FIGS. 17A-17F show the ABS staining results of cerebroside sulfate substrate levels in brain tissue of mARSA-deficient mice after treatment with hARSA-9056VHH.
Figure 17D:
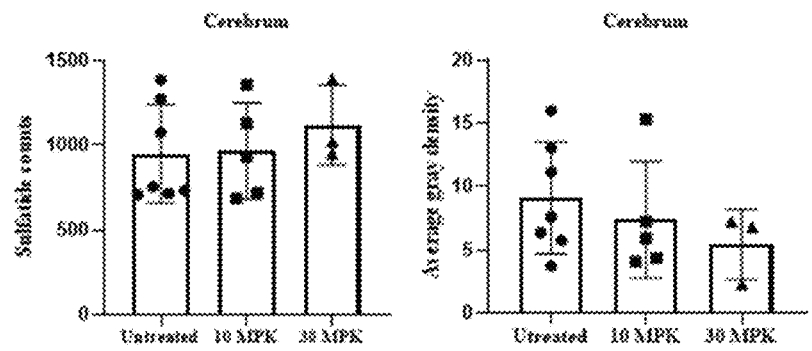
Figure 17E:
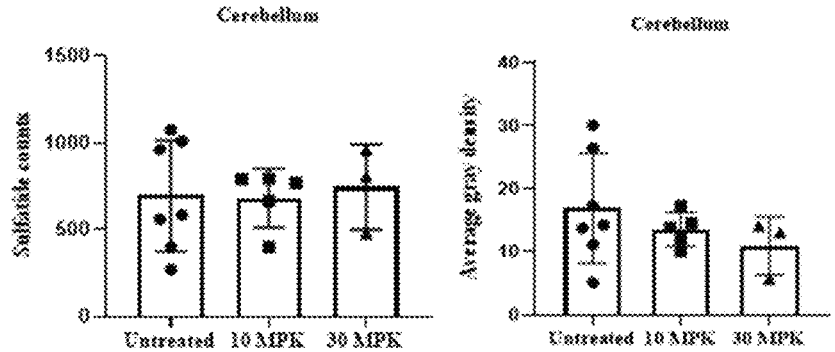
Figure 17F:
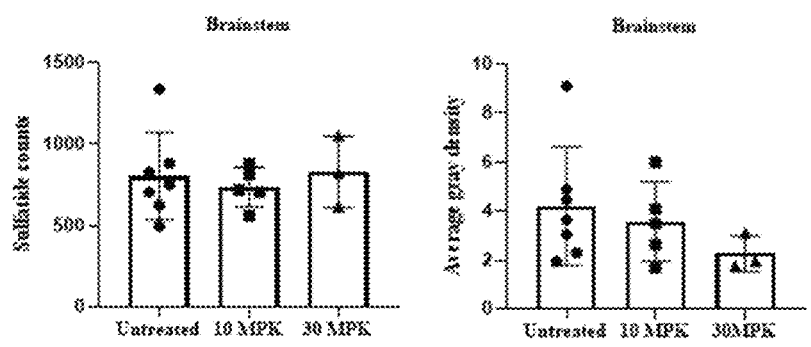

3) The time of mice passing through the balance beam in each group was analyzed. The results are shown in FIG. 15. In BIW×8 group, after 4 weeks of treatment of the 30 MPK, the time for mice to pass through the balance beam is significantly reduced (83.53%) as compared with the time to pass through the balance beam before administration. P<0.001 (Dunnett's multiple comparisons).

7.2.4 Sample Collection

On day 32 (8 days after the last administration), mice were euthanized, and 0.2 mL of urine was collected (4 hours before euthanasia). The collected urine was stored at −20° C. for further test. Whole blood was collected by puncturing at the orbital sinus venous plexus and placed in a serum preparation tube. After 10 minutes, the collected blood was centrifuged at 3000 g for 5 minutes. The supernatant was collected into 1.5 mL centrifuge tube and stored at −80° C.

Tissue organs were also collected and stored at −80° C. Brain (including olfactory bulb, cerebellum, cerebrum, brain stem and part of the spinal cord) was sagittally cut. Left brain (divided into the cerebellum, cerebrum, brain stem and part of the spinal cord) and left kidney were stored in liquid nitrogen for TLC and ELISA detection. Right brain and right kidney were fixed with 4% PFA for alcian blue staining and immunofluorescence staining. The sciatic nerve was fixed with 4% PFA for Alcian Blue staining.

7.2.5 Sample Analysis

7.2.5.1 Analysis of Cerebroside Sulfate in Brain (1) Thin-layer chromatography analysis of sulfatide/GalCer ratio: Weigh 100 mg mouse cerebrum, 20 mg cerebellum, 20 mg brain stem from each group. According to the weight-volume ratio of 1:5, the tissues were added with 1 mL or 200 μL of TBS (pH7.4), respectively. Homogenized with steel beads at 60 HZ for 60 s. The homogenate was replenished to 2 mL and centrifuged at 13,000 rpm for 2 hours at 4° C. The supernatant was discarded and the precipitate were collected for lipid extraction. The precipitate was added with 5 mL $CH_3Cl/CH_3OH$ (2:1) and extracted at 60° C. for 4 hours. The solvent supernatant was centrifuged and then transferred. The precipitate was extracted with 5 mL C/M (1:1) at 60° C. for 4 hours. The extracts from the two crude extracts were combined, mixed well and taken half for the subsequent operation and the other half was left as the control. 5 mL of the extracts were taken to spin drying until the white adherent material is visible. The dried extracts were dissolved with 5 mL of MeOH, added with 250 μL of 4N NaOH and incubated at 37° C. for 2 hours. The reaction was stopped with 40 μL of 100% acetic acid. The solvent was evaporated, and 1 mL of MeOH was added to dissolve. The solution was then added with 1 mL of 0.3M ammonium acetate solution for further use. Desalting: Approximately 1 mL of ODS (MeOH preactivated) filled the column (YMC, Japan, AAG12S50) and the column was equilibrated with 6 mL of mixed solvent: C/M/0.1 M KCl 6:96:94. The aforesaid resulted solution was added into the column and washed with 6 mL $H_2O$ for desalting, then eluted with 1 mL MeOH and 6 mL C/M (1:1), wherein white turbidity appeared in the elution process, and then gradually disappeared. Concentration: The eluate containing lipid molecules was evaporated by a rotary evaporator (Shanghai Bochu Instrument Co., Ltd., LOOYE), and finally fully dissolved with 500 μL of C/M 2:1 for TLC analysis. A certain volume of sample was uploaded to the silica gel plate. Sulfatide (Matreya LLC; Cat.NO.: 1049-50 mg; Lot No.: 24534) and GalCer (Matreya LLC; Cat.NO.: 1066-10 mg; Lot No.: 23332) were used for the standard. Developing time is about 10 minutes. Developing solvent: chloroform:methanol:water 65:25:4 (v/v/v) (need to be prepared in advance to saturate the inside of the TLC chamber with vapor). $CuSO4$ staining: The TLC silica gel plate was immersed in the color development solution (10% CuSO4 in 10% phosphoric acid solution) for about 3 mins. Dried the plate and placed it in the oven at 130° C. for 10 mins, until black spots or bands were appeared. The plate was scanned by gel imager and the images were analyzed. The sulfatide/GalCer ratio was calculated for each group of mouse brain tissues, mean±SD. As shown in FIGS. 16A-16F: in the treated mARSA$^{-/-}$ mice, after intravenously administration (BIW) for 4 weeks, the sulfatide substrate accumulation in the brain (FIG. 16A, FIG. 16B), cerebellum (FIG. 16C, FIG. 16D), and brainstem (FIG. 16E, FIG. 16F) was significantly decreased, and shown a dose-dependent manner (p-values=0.027, 0.026, and 0.059, respectively; by One-way ANOVA).

(2) Alcian blue staining: Frozen 10 μm sagittal sections of brain tissue were prepared (by Shanghai Ribiology Biological Co., Ltd.). Alcian blue staining buffer (0.025 M sodium acetate, pH 5.7, containing 0.3 M $MgCl_2$, 1% PFA) was prepared, and 0.05% Alisin blue (Alisin blue 8GX, sigma, A9186-10G) was dissolved in the staining buffer. Frozen sections of brain tissue were fixed with 4% paraformaldehyde (PFA) for 1 minute, and then washed with staining buffer. 0.05% Alcian Blue staining solution was incubated for 1 hour at room temperature. Fast red counter staining was performed for 2 minutes. The slides were sealed with glycerol. The photographs were taken for observation under the microscope. The results are shown in FIGS. 17A-17F. In the treated mARSA$^{-/-}$ mice, after intravenously administration (BIW) for 4 weeks, there is no significant difference in the amount of substrate sulfatide accumulation in the cerebrum (B1, C1, FIG. 17D), cerebellum (B3, C3, FIG. 17E) and brainstem (B2, C2, FIG. 17F) in the 10 MPK (FIG. 17B) and 30 MPK (FIG. 17C) groups. The average gray densities were reduced in a dose-dependent manner in 10 MPK and 30 MPK groups compared with the untreated group.

7.2.5.2 Sulfatides in Sciatic Nerve

The same method described in 7.2.5.1 for detecting cerebroside sulfate substrates in the sciatic nerve was used. The deposition of cerebroside sulfate substrates in the treated and untreated groups of mice was analyzed by Alcian Blue staining and thin-layer chromatography with sulfatide/cholesterol ratio. The results are shown in FIGS. 18A-18F. FIG. 18A: The TLC results show that in mARSA$^{-/-}$ mice treated with intravenously administration (BIW) for 4 weeks, sulfatide accumulation in sciatic nerve was significantly decreased in both 10 and 30 MPK groups in a dose-dependent manner (P values being less than the 0.0001, by One-way ANOVA). FIG. 18B: The results of the ABS staining are consistent with that of the TLC results. The sulfatide accumulation was significantly reduced in both the 10 and 30 MPK groups in a dose-dependent manner (P values are 0.033, 0.032, by One-way ANOVA, respectively).

7.2.5.3 Sulfatides in Kidney

Figure 19A:
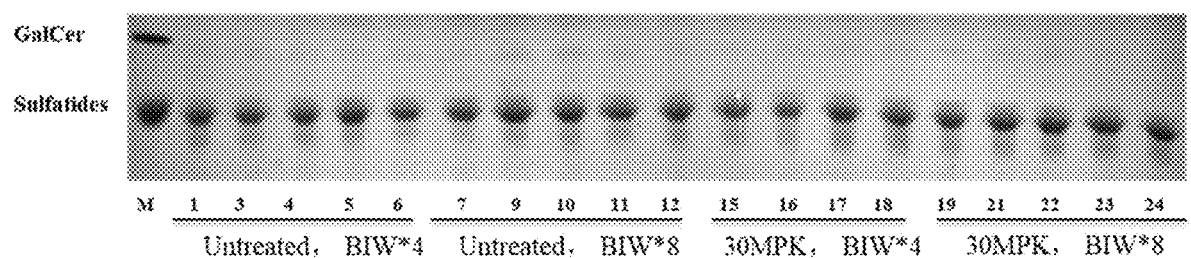
FIGS. 19A and 19B show the cerebroside sulfate substrate levels in the kidneys of mARSA-deficient mice after treatment with hARSA-9056VHH.
Figure 19B:
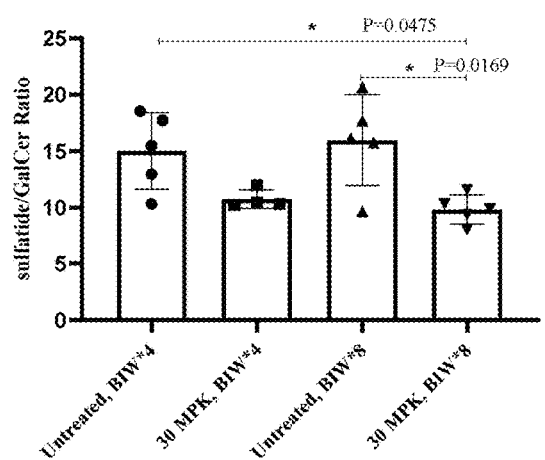

The same experimental method of detecting cerebroside sulfate substrates in the kidney tissue was used as described in 7.2.5.1. The deposition of cerebroside sulfate in the treated and untreated groups of mice was analyzed by thin-layer chromatography with sulfatide/cholesterol ratio. The results are shown in FIGS. 19A-19B: after 2 weeks of treatment, the cerebroside sulfate in treated group (30 MPK, BIW×4) was decreased compared with untreated group. But there was no statistically significant difference. After 4 weeks of treatment, the level of cerebroside sulfate substrate in treated group (30 MPK, BIW×8) was significantly decreased compared with untreated group (P=0.0169, One-way ANOVA).

SEQUENCE LISTING

```
Sequence total quantity: 12
SEQ ID NO: 1                 moltype = AA   length = 5
FEATURE                      Location/Qualifiers
source                       1..5
                             mol_type = protein
                             organism = synthetic construct
SEQUENCE: 1
GNYMG                                                                        5

SEQ ID NO: 2                 moltype = AA   length = 17
FEATURE                      Location/Qualifiers
source                       1..17
                             mol_type = protein
                             organism = synthetic construct
SEQUENCE: 2
VLYTGGGSTY YADSVKG                                                          17

SEQ ID NO: 3                 moltype = AA   length = 19
FEATURE                      Location/Qualifiers
source                       1..19
                             mol_type = protein
                             organism = synthetic construct
SEQUENCE: 3
ALGSARWYTS SLDARAYNI                                                        19

SEQ ID NO: 4                 moltype = AA   length = 30
FEATURE                      Location/Qualifiers
source                       1..30
                             mol_type = protein
                             organism = synthetic construct
SEQUENCE: 4
EVQLVESGGG LVQPGGSLRL SCAASGHAYG                                            30

SEQ ID NO: 5                 moltype = AA   length = 14
FEATURE                      Location/Qualifiers
source                       1..14
                             mol_type = protein
                             organism = synthetic construct
SEQUENCE: 5
WFRQAPGKGL EGVA                                                             14

SEQ ID NO: 6                 moltype = AA   length = 32
FEATURE                      Location/Qualifiers
source                       1..32
                             mol_type = protein
                             organism = synthetic construct
SEQUENCE: 6
RFTISEDNSK NTVYLQMNSL RAEDTAVYYC AL                                         32

SEQ ID NO: 7                 moltype = AA   length = 11
FEATURE                      Location/Qualifiers
source                       1..11
                             mol_type = protein
                             organism = synthetic construct
SEQUENCE: 7
WGQGTLVTVS S                                                                11

SEQ ID NO: 8                 moltype = AA   length = 128
FEATURE                      Location/Qualifiers
source                       1..128
                             mol_type = protein
                             organism = synthetic construct
SEQUENCE: 8
EVQLVESGGG LVQPGGSLRL SCAASGHAYG GNYMGWFRQA PGKGLEGVAV LYTGGGSTYY           60
ADSVKGRFTI SEDNSKNTVY LQMNSLRAED TAVYYCALAL GSARWYTSSL DARAYNIWGQ          120
GTLVTVSS                                                                  128

SEQ ID NO: 9                 moltype = AA   length = 15
FEATURE                      Location/Qualifiers
source                       1..15
                             mol_type = protein
                             organism = synthetic construct
SEQUENCE: 9
GGGGSGGGGS GGGGS                                                            15

SEQ ID NO: 10                moltype = AA   length = 489
FEATURE                      Location/Qualifiers
source                       1..489
```

```
                        mol_type = protein
                        organism = synthetic construct
SEQUENCE: 10
RPPNIVLIFA  DDLGYGDLGC  YGHPSSTTPN  LDQLAAGGLR  FTDFYVPVSL  CTPSRAALLT   60
GRLPVRMGMY  PGVLVPSSRG  GLPLEEVTVA  EVLAARGYLT  GMAGKWHLGV  GPEGAFLPPH  120
QGFHRFLGIP  YSHDQGPCQN  LTCFPPATPC  DGGCDQGLVP  IPLLANLSVE  AQPPWLPGLE  180
ARYMAFAHDL  MADAQRQDRP  FFLYYASHHT  HYPQFSGQSF  AERSGRGPFG  DSLMELDAAV  240
GTLMTAIGDL  GLLEETLVIF  TADNGPETMR  MSRGGCSGLL  RCGKGTTYEG  GVREPALAFW  300
PGHIAPGVTH  ELASSLDLLP  TLAALAGAPL  PNVTLDGFDL  SPLLLGTGKS  PRQSLFFYPS  360
YPDEVRGVFA  VRTGKYKAHF  FTQGSAHSDT  TADPACHASS  SLTAHEPPLL  YDLSKDPGEN  420
YNLLGGVAGA  TPEVLQALKQ  LQLLKAQLDA  AVTFGPSQVA  RGEDPALQIC  CHPGCTPRPA  480
CCHCPDPHA                                                               489

SEQ ID NO: 11           moltype = AA  length = 643
FEATURE                 Location/Qualifiers
source                  1..643
                        mol_type = protein
                        organism = synthetic construct
SEQUENCE: 11
RPPNIVLIFA  DDLGYGDLGC  YGHPSSTTPN  LDQLAAGGLR  FTDFYVPVSL  CTPSRAALLT   60
GRLPVRMGMY  PGVLVPSSRG  GLPLEEVTVA  EVLAARGYLT  GMAGKWHLGV  GPEGAFLPPH  120
QGFHRFLGIP  YSHDQGPCQN  LTCFPPATPC  DGGCDQGLVP  IPLLANLSVE  AQPPWLPGLE  180
ARYMAFAHDL  MADAQRQDRP  FFLYYASHHT  HYPQFSGQSF  AERSGRGPFG  DSLMELDAAV  240
GTLMTAIGDL  GLLEETLVIF  TADNGPETMR  MSRGGCSGLL  RCGKGTTYEG  GVREPALAFW  300
PGHIAPGVTH  ELASSLDLLP  TLAALAGAPL  PNVTLDGFDL  SPLLLGTGKS  PRQSLFFYPS  360
YPDEVRGVFA  VRTGKYKAHF  FTQGSAHSDT  TADPACHASS  SLTAHEPPLL  YDLSKDPGEN  420
YNLLGGVAGA  TPEVLQALKQ  LQLLKAQLDA  AVTFGPSQVA  RGEDPALQIC  CHPGCTPRPA  480
CCHCPDPHAG  GGGSGGGGSG  GGGSEVQLVE  SGGGLVQPGG  SLRLSCAASG  HAYGGNYMGW  540
FRQAPGKGLE  GVAVLYTGGG  STYYADSVKG  RFTISEDNSK  NTVYLQMNSL  RAEDTAVYYC  600
ALALGSARWY  TSSLDARAYN  IWGQGTLVTV  SSGGGGSHHH  HHH                     643

SEQ ID NO: 12           moltype = AA  length = 129
FEATURE                 Location/Qualifiers
source                  1..129
                        mol_type = protein
                        organism = synthetic construct
SEQUENCE: 12
HVQLVESGGG  SVQAGGSLRL  SCVASGIGHG  FNNNCMGWFR  QAPGKEREGV  AAVYTGGGTP   60
YYADSVKGRF  TLSQDNAKNT  LYLQMNGLDP  EDTAMYYCVA  DIWRTYRCGA  GDTTVFDYRG  120
QGTLVTVSS                                                               129
```

What is claimed is:

1. A fusion protein comprising: (a) a transferrin-binding protein, and (b) an arylsulfatase A (ARSA) or functionally active fragment thereof, wherein the transferrin-binding protein is a VHH capable of binding transferrin, wherein the VHH comprises a CDR1 of SEQ ID NO: 1, a CDR2 of SEQ ID NO: 2 and a CDR3 of SEQ ID NO: 3.

2. The fusion protein of claim 1, wherein the fusion protein exhibits one or more properties selected from the group consisting of:
   1. Capable of extending in vivo half-life of ARSA;
   2. Capable of crossing blood brain barriers (BBB);
   3. capable of being delivered orally;
   4. capable of delivering the ARSA to a cell expressing transferrin receptor; and
   5. capable of binding transferrin and catalyze the degradation of cerebroside sulfate which is a substrate of the ARSA.

3. The fusion protein of claim 1, wherein the VHH comprises SEQ ID NO: 8.

4. The fusion protein of claim 1, wherein the ARSA is human ARSA.

5. The fusion protein of claim 1, wherein the ARSA or the functionally active fragment thereof comprises SEQ ID NO: 10.

6. The fusion protein of claim 1, wherein the transferrin-binding protein is directly or indirectly linked to the ARSA or the functionally active fragment thereof.

7. The fusion protein of claim 1, wherein the N-terminal of the transferrin-binding protein is directly or indirectly linked to the C-terminal of the ARSA or the functionally active fragment thereof.

8. The fusion protein of claim 1, wherein the C-terminal of the transferrin-binding protein is directly or indirectly linked to the N-terminal of the ARSA or the functionally active fragment thereof.

9. The fusion protein of claim 1, wherein the transferrin-binding protein is linked to the ARSA or the functionally active fragment thereof through a linker moiety.

10. The fusion protein of claim 9, wherein the linker moiety comprises a peptide linker.

11. The fusion protein of claim 9, wherein the linker moiety comprises SEQ ID NO: 9.

12. The fusion protein of claim 1, comprising SEQ ID NO: 11.

13. An isolated nucleic acid molecule encoding the fusion protein of claim 1.

14. A vector comprising the nucleic acid molecule of claim 13.

15. A cell comprising the nucleic acid molecule of claim 13.

16. A pharmaceutical composition comprising the fusion protein of claim 1, and a pharmaceutically acceptable carrier.

17. A method for treating a disease and/or disease-related symptoms caused by ARSA abnormalities, comprising administering to a subject in need thereof the fusion protein of claim 1, wherein the disease is Metachromatic Leukodystrophy (MLD).

18. A method for delivering an ARSA to cross the BBB, comprising administering the fusion protein of claim 1.

* * * * *